(12) United States Patent
Niitsu

(10) Patent No.: US 11,347,083 B2
(45) Date of Patent: May 31, 2022

(54) MEASURING DEVICE, CONTAINER DEVICE, AND MEASURING SYSTEM

(71) Applicant: JAPAN SCIENCE AND TECHNOLOGY AGENCY, Kawaguchi (JP)

(72) Inventor: Kiichi Niitsu, Nagoya (JP)

(73) Assignee: JAPAN SCIENCE AND TECHNOLOGY AGENCY, Kawaguchi (JP)

( * ) Notice: Subject to any disclaimer, the term of this patent is extended or adjusted under 35 U.S.C. 154(b) by 0 days.

(21) Appl. No.: 17/052,583

(22) PCT Filed: May 15, 2019

(86) PCT No.: PCT/JP2019/019265
§ 371 (c)(1),
(2) Date: Nov. 3, 2020

(87) PCT Pub. No.: WO2019/221166
PCT Pub. Date: Nov. 21, 2019

(65) Prior Publication Data
US 2021/0240014 A1 Aug. 5, 2021

(30) Foreign Application Priority Data

May 15, 2018 (JP) .............................. JP2018-093952
Jan. 25, 2019 (JP) .............................. JP2019-010727

(51) Int. Cl.
*G08B 21/00* (2006.01)
*G02C 11/00* (2006.01)
(Continued)

(52) U.S. Cl.
CPC .......... *G02C 11/10* (2013.01); *A61B 5/14532* (2013.01); *A61B 5/6803* (2013.01); *G02C 7/04* (2013.01); *H04B 5/0031* (2013.01)

(58) Field of Classification Search
CPC ....... G02C 11/10; G02C 7/04; A61B 5/14532; A61B 5/6803; H04B 5/0031
See application file for complete search history.

(56) References Cited

U.S. PATENT DOCUMENTS

2006/0152200 A1* 7/2006 Kanai .................. H02M 3/156
323/222
2016/0154256 A1* 6/2016 Yajima ................ G02B 27/017
600/347

(Continued)

FOREIGN PATENT DOCUMENTS

| JP | 2017-125914 A | 7/2017 |
| JP | 2018-105954 A | 7/2018 |
| WO | 2015/022868 A1 | 2/2015 |

OTHER PUBLICATIONS

International Search Report dated Jul. 30, 2019, issued in counterpart application No. PCT/JP2019/019265, w/English translation (9 pages).

(Continued)

*Primary Examiner* — Mark S Rushing
(74) *Attorney, Agent, or Firm* — WHDA, LLP

(57) ABSTRACT

The Present invention is a measuring system including a measuring device 10 that is attached to a living body, the measuring device 10 being configured to store information about an amount of electric power generated using sugars in a body fluid or bodily secretion of a living body, and a container device 15 for storing the measuring device 10, the container device 15 receiving the information about the amount of electric power generated, which is stored in the measuring device 10, using a near-field wireless communication method when the measuring device 10 is stored in the container device 15.

14 Claims, 29 Drawing Sheets

(51) Int. Cl.
*A61B 5/145* (2006.01)
*A61B 5/00* (2006.01)
*G02C 7/04* (2006.01)
*H04B 5/00* (2006.01)

(56) References Cited

U.S. PATENT DOCUMENTS

2017/0173262 A1* 6/2017 Veltz .................... A61B 5/0022
2018/0136492 A1* 5/2018 An ....................... A61B 5/6821

OTHER PUBLICATIONS

Written Opinion dated Jul. 30, 2019, issued in counterpart application No. PCT/JP2019/019265 (9 pages).
Ishizaki et al., "A Battery-less WiFi-BER modulated data transmitter with ambient radio-wave energy harvesting", 2011 Symposium on VLSI Circuits Digest of Technical Papers, Jun. 17, 2011, pp. 162-163, cited in ISR (2 pages).
Niitsu, "An energy-generation-and-sensing-combined integrated biosensor platform using low-power CMOS integrated circuits system and bio fuel cells for innovation of Diabetes treatment and prevention", Proceedings of the 2018 of IEICE general conference, Mar. 23, 2018, pp. SS42-SS43, cited in ISR, w/English translation (5 pages).
Kobayashi et al., "Design and Experimental Verification of a 0.19 V 53 µW 65 nm CMOS Integrated Supply-Sensing Sensor With a Supply-Insensitive Temperature Sensor and an Inductive-Coupling Transmitter for a Self-Powered Bio-sensing System Using a Biofuel Cell", IEEE Transactions on Biomedical Circuits and Systems, 2017, pp. 1-11, cited in ISR (11 pages).
Fojtik et al., "A Millimeter-Scale Energy-Autonomous Sensor System With Stacked Battery and Solar Cells", IEEE Journal of Solid-State Circuits, Mar. 2013, vol. 48, No. 3, pp. 801-813 (13 pages).
Aiello et al., "A Sub-Leakage pW-Power Hz-Range Relaxation Oscillator Operating with 0.3 V-1.8V Unregulated Supply", 2018 IEEE Symposium on VLSI Circuits Digest of Technical Papers, pp. 119-120 (2 pages).
Paidimarri et al., "A +10 dBm BLE Transmitter With Sub-400 pW Leakage for Ultra-Low Duty Cycles", IEEE Jornal of Solid-State Circuits, Jun. 2016, vol. 51, No. 6, pp. 1331-1346 (16 pages).
Yang et al., "A 0.6nJ −0.22/+0.19° C. Inaccuracy Temperature Sensor Using Exponential Subthreshold Oscillation Dependence", 2017 IEEE International Solid-State Circuits Conference, Feb. 2017, pp. 160-161 (3 pages).
Patel et al., "A 55nm Ultra Low Leakage Deeply Depleted Channel Technology Optimized for Energy Minimization in Subthreshold SRAM and Logic", ESSCIRC Conference 2016: 42nd European Solid-State Circuits Conference, Sep. 12-15, 2016, pp. 37-40 (4 pages).
Jeong et al., "A Fully-Integrated 71 nW CMOS Temperature Sensor for Low Power Wireless Sensor Nodes", IEEE Journal of Solid-State Circuits, Aug. 2014, vol. 49, No. 8, pp. 1682-1693 (12 pages).
El-Bayoumi et al., "A New Highly-Linear Highly-Sensitive Differential Voltage-to-Time Converter Circuit in CMOS 65nm Technology", 2015 IEEE International Symposium on Circuits and Systems, May 24-27, 2015, pp. 1262-1265 (4 pages).
Wang et al., "A Reference-Free Capacitive-Discharging Oscillator Architecture Consuming 44.4 pW/75.6 nW at 2.8 Hz/6.4 kHz", IEEE Journal of Solid-State Circuits, Jun. 2016, vol. 51, No. 6, pp. 1423-1435 (13 pages).
O'Halloran et al., "An Analog Storage Cell with 5e⁻/sec Leakage", 2006 IEEE International Symposium on Circuits and Systems, May 21-24, 2006, pp. 557-560 (4 pages).

* cited by examiner

MEASURING DEVICE, CONTAINER DEVICE, AND MEASURING SYSTEM

TECHNICAL FIELD

The present invention relates to a measuring device, a container device, and a measuring system, for example, to a measuring device for measuring sugars or biomolecules, a container device, and a measuring system.

BACKGROUND ART

There has been known a biomolecule detection device that includes a power generation unit that is provided to a contact lens or the like and utilizes the decomposition reaction of biomolecules such as sugars, and transmits radio signals at a frequency based on the power generation amount of the power generation unit (for example, Patent Document 1).

PRIOR ART DOCUMENT

Patent Document

Patent Document 1: Japanese Patent Application Publication No. 2017-125914

SUMMARY OF THE INVENTION

Problem to be Solved by the Invention

In Patent Document 1, the electric power generated using the decomposition reaction of the biomolecule is used and therefore it is not necessary to supply electric power from the outside. However, the power consumption of the transmission circuit for transmitting radio signals in real time may be large, and the electric power generated by the power generation unit may be insufficient.

The present invention has been made in view of above problems, and an objective thereof is to reduce the power consumption of the measuring device.

Means for Solving the Problem

The present invention is a measuring system including: a measuring device that is attached to a living body, the measuring device being configured to store information about an amount of electric power generated using sugars in a body fluid or bodily secretion of a living body; and a container device for storing the measuring device, the container device receiving the information about the amount of electric power generated, which is stored in the measuring device, using a near-field wireless communication method when the measuring device is stored in the container device.

In the above configuration, the measuring device may be configured to use an electric power generated using sugars in the body fluid or bodily secretion of the living body as a power supply to generate and store the information about the amount of electric power generated.

In the above configuration, the container device may include a first antenna and a second antenna, the measuring device may include a third antenna to be sandwiched between the first antenna and the second antenna when the measuring device is stored in the container device, and the measuring device may transmit the information to the container device by the third antenna inhibiting electromagnetic coupling between the first antenna and the second antenna or propagation of an electromagnetic wave.

In the above configuration, the measuring device may include: a power generation unit that generates an electromotive force through a reaction of the sugars, a first oscillator that uses the electromotive force of the power generation unit as a power-supply voltage, and generates a first oscillation signal of which a period varies in response to a variation in the electromotive force, a second oscillator that uses the electromotive force as a power-supply voltage and generates a second oscillation signal of which a variation in period with respect to a variation in the electromotive force is smaller than that of the first oscillator, a timing circuit that uses the electromotive force as a power-supply voltage and generates a first timing and a second timing according to the second oscillation signal, a counter circuit that uses the electromotive force as a power-supply voltage, and counts the number of pulses of the first oscillation signal between the first timing and the second timing, and a storage unit that stores the number of pulses as the information.

In the above configuration, the measuring device may be mounted to a contact lens, and the body fluid or bodily secretion of the living body is a tear.

The present invention is a measuring device to be attached to a living body, including: a power generation unit that generates electric power using sugars in a body fluid or bodily secretion of the living body; a storage unit that stores information about a power generation amount of the power generation unit; and a transmission unit that transmits the information about the power generation amount stored in the storage unit to a container device using a near-field wireless communication method when the measuring device is stored in the container device.

The present invention is a container device including: a container unit for storing a measuring device to be attached to a living body, the measuring device storing information about an amount of electric power generated using sugars in a body fluid or bodily secretion of the living body; and a reception unit that receives the information about the amount of electric power generated, which is stored in the measuring device, using a near-field wireless communication method when the measuring device is stored in the container unit.

The present invention is a measuring device including: a power generation unit that generates an electromotive force through a reaction of biomolecules; a first oscillator that uses the electromotive force as a power-supply voltage and generates a first oscillation signal of which a period varies in response to a variation in the electromotive force; a second oscillator that uses the electromotive force as a power-supply voltage and generates a second oscillation signal of which a variation in period with respect to a variation in the electromotive force is smaller than that of the first oscillator; and a timing circuit that uses the electromotive force as a power-supply voltage and generates a first timing and a second timing according to the second oscillation signal; and a counter circuit that uses the electromotive force as a power-supply voltage and counts the number of pulses of the first oscillation signal between the first timing and the second timing.

In the above configuration, a memory circuit that stores information on the number of pulses may be provided.

In the above configuration, a transmission circuit that transmits the information about the number of pulses stored in the memory circuit using a near-field wireless communication method may be provided.

In the above configuration, an electricity storage device that accumulates electric power generated by the power generation unit, and supplies an electric power for retaining the information about the number of pulses stored in the memory circuit to the memory circuit when the power generation unit does not generate electric power may be provided.

The present invention is a measuring device to be attached to a living body, including: a power generation unit that generates a first electromotive force using sugars in a body fluid or bodily secretion of the living body; a conversion circuit that uses the first electromotive force as a power-supply voltage and converts the first electromotive force into a digital signal; a transmission circuit that transmits information about the digital signal using a wireless communication method; and a power supply that supplies electric power to the transmission circuit without supplying electric power to the conversion circuit.

In the above configuration, the power supply may be a solar cell.

In the above configuration, a booster circuit that is activated according to an activation signal generated by the conversion circuit and boosts a second electromotive force generated by the solar cell may be provided.

The present invention is a measuring device including: a power generation unit that generates an electromotive force through a reaction of biomolecules; an oscillator that uses the electromotive force as a power-supply voltage and generates an oscillation signal; a voltage-time conversion circuit that uses the electromotive force as a power-supply voltage and converts a magnitude of the electromotive force into a period; and a counter circuit that uses the electromotive force as a power-supply voltage and counts the number of pulses of the oscillation signal within the period.

Effects of the Invention

The present invention reduces the power consumption of a measuring device.

Hereinafter, with reference to the accompanying drawings, embodiments will be described.

FIRST EMBODIMENT

Figure 1A:
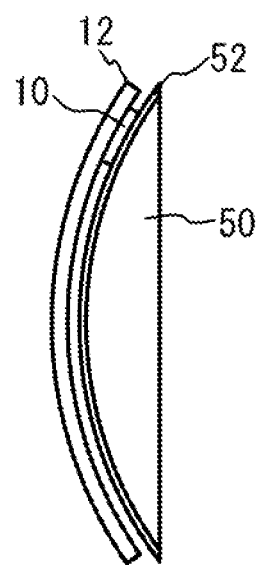
FIG. 1A and FIG. 1B are schematic views of a measuring system in accordance with a first embodiment.
Figure 1B:
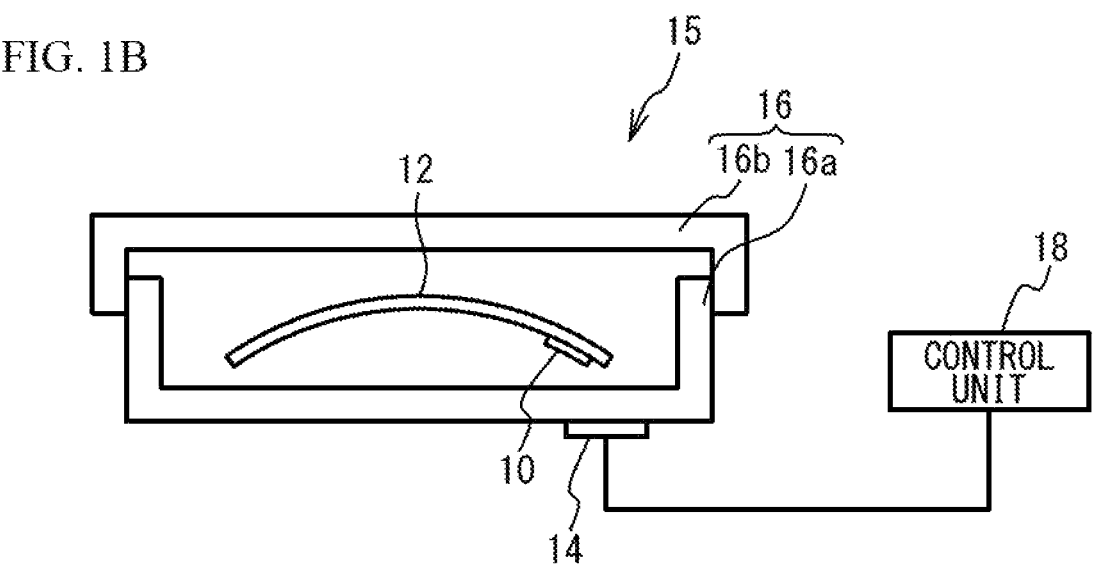
Figure 2:
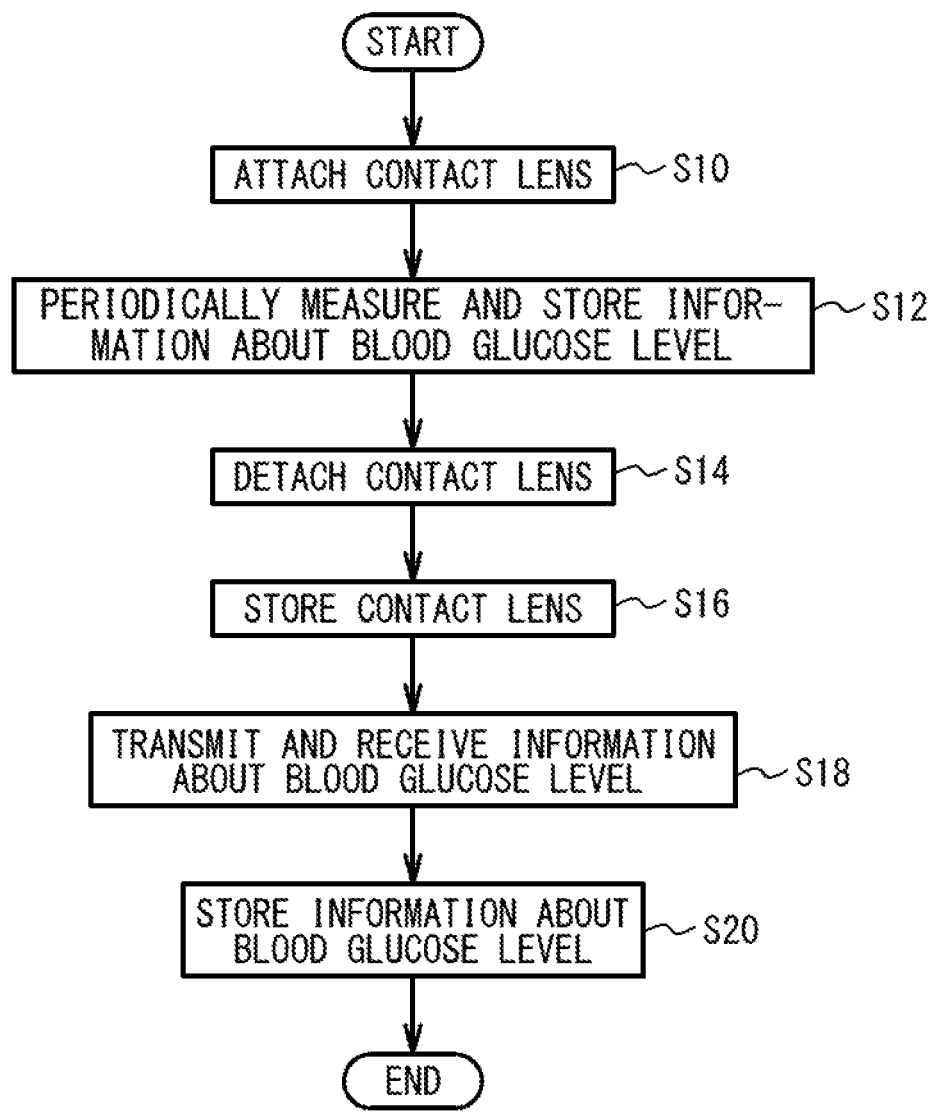
FIG. 2 is a flowchart of a method for measuring a blood glucose level in the first embodiment.

FIG. 1A and FIG. 1B are schematic views of a measuring system accordance with a first embodiment. FIG. 1A illustrates a state where a contact lens is attached to the eye of a user, and FIG. 1B illustrates the contact lens stored in a container device. FIG. 2 is a flowchart of a method for measuring a blood glucose level in the first embodiment.

As illustrated in FIG. 1A, a contact lens 12 quipped with a measuring device 10. In step S10 of FIG. 2, the user attaches the contact lens 12 onto the eye. The contact lens 12 is attached to the cornea 50 of the user.

In step S12 of FIG. 2, the measuring device 10 periodically measures information about the blood glucose level of the user. For example, the measuring device 10 periodically measures the glucose concentration in a tear 52 on the surface of the cornea 50. The measuring device 10 stores the information about the glucose concentration in the tear 52 continuously measured. The glucose concentration in the tear 52 correlates with the glucose concentration in the blood. Thus, the glucose concentration (i.e., the blood glucose level) in the blood can be estimated by measuring the glucose concentration in the tear 52. The glucose concentration is measured at intervals of, for example, one second to several minutes.

In step S14 of FIG. 2, the user detaches the contact lens 12 from the eye. For example, the user does not wear the contact lens 12 during sleeping. The user may detach the contact lens 12 to clean the contact lens 12.

As illustrated in FIG. 1B, a container device 15 includes a container unit 16 and a reception unit 14. The container unit 16 includes a bottom portion 16a and a lid portion 16b. In step S16 of FIG. 2, the user stores the contact lens 12 in the container unit 16 of the container device 15. For example, the user stores the contact lens 12 in the recessed portion of the bottom portion 16a, and covers the bottom portion 16a with the lid portion 16b.

In step S18 of FIG. 2, the reception unit 14 receives the information about the blood glucose level (for example, the glucose concentration) stored in the measuring device 10 using a near-field wireless communication method. The near-field wireless communication method is, for example, near field communication (NFC), and is an electromagnetic coupling type communication method or an electromagnetic wave type communication method. The transmission range between the measuring device 10 and the reception unit 14 is, for example, 10 cm or less.

In step S20 of FIG. 2, the reception unit 14 transmits the received information to a control unit 18 such as a computer. The control unit 18 stores temporal change in the blood glucose level of the user in a server or the like. Thereafter, the primary doctor or the like can access the data about the blood glucose level of the user.

Body fluids or bodily secretions from which the blood glucose level can be measured are blood, cutaneous intercellular fluids, tears, saliva, sweat, and urine. The accuracy of the blood glucose level becomes lower in this order, and when a body fluid or bodily secretion other than blood is used, it may take a long time for the blood glucose level in the body fluid or bodily secretion other than blood to become the same as the blood glucose level in the blood. Therefore, the blood glucose level is measured using a continuous glucose measurement system (CGMS). However, the CGMS requires a needle to be inserted into the body of the user, which may cause the user to take action in consideration of the measurement of the blood glucose level. This makes it impossible to measure the blood glucose level during normal times. For this reason, in the first embodiment, the glucose concentration in a tear is measured using a contact lens type measuring device. This allows the blood glucose level to be continuously measured precisely without making the user be conscious of the measurement.

Figure 3:
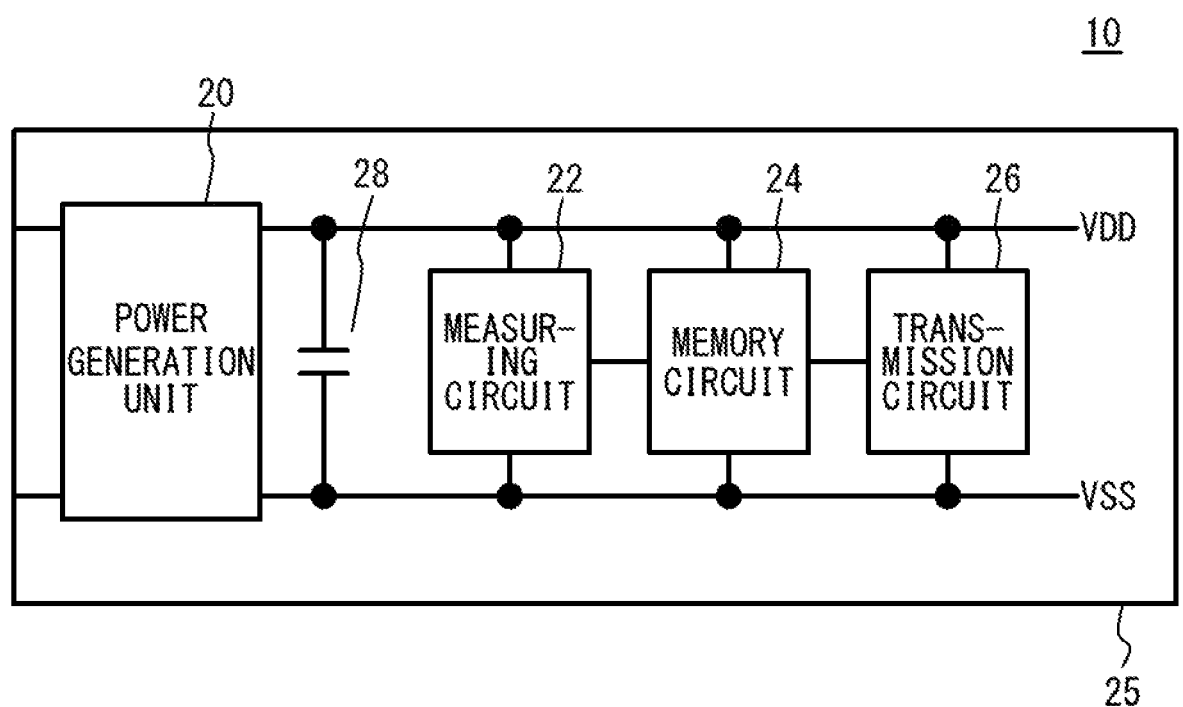
FIG. 3 is a block diagram of a measuring device in the first embodiment.

FIG. 3 is a block diagram of a measuring device in the first embodiment. As illustrated in FIG. 3, the measuring device 10 includes a power generation unit 20, a measuring circuit 22, a memory circuit 24, a transmission circuit 26, and an electricity storage device 28. The power generation unit 20 generates electric power using electromotive force generated through the decomposition reaction of glucose in tears. The power generation unit 20 supplies the electromotive force to the measuring circuit 22, the memory circuit 24, and the transmission circuit 26 as a power-supply voltage (voltage VDD-voltage VSS). The electricity storage device 28 is, for example, a capacitor, and accumulates the electric power generated by the power generation unit 20. The electricity storage device 28 may not be necessarily provided.

The measuring circuit 22 generates information related to the magnitude of the power-supply voltage corresponding to the electromotive force of the power generation unit 20. The memory circuit 24 stores the information generated by the measuring circuit 22. The memory circuit 24 is, for example, a volatile memory such as a static random-access memory (SRAM) or a nonvolatile memory such as a flash memory. To allow the memory circuit 24 to retain the information when the power generation unit 20 does not generate electric power (for example, the contact lens 12 is detached), the memory circuit 24 is preferably a nonvolatile memory. However, the nonvolatile memory needs high voltage when writing and reading the information. Thus, the memory circuit 24 may be a volatile memory. When the memory circuit 24 is a volatile memory and the power generation unit 20 does not generate electric power, the memory circuit 24 uses the electric power stored in the electricity storage device 28 to retain the information.

The transmission circuit 26 transmits the information stored in the memory circuit 24 to the reception unit 14 of the container device 15 using a near-field wireless communication method. The power generation unit 20, the measuring circuit 22, the memory circuit 24, the transmission circuit 26, and the electricity storage device 28 are formed of, for example, a semiconductor integrated circuit provided on a substrate 25.

Figure 4:
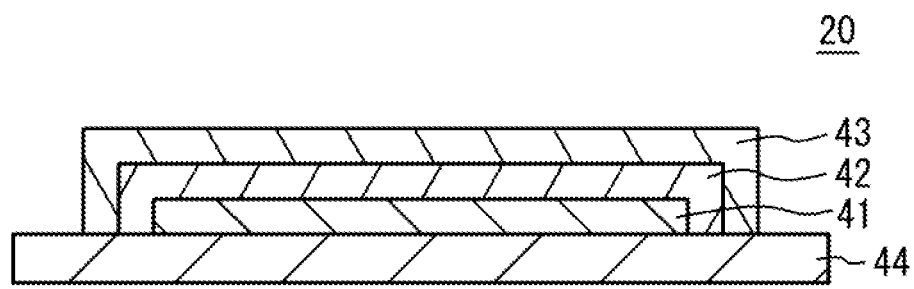
FIG. 4 is a cross-sectional view of a power generation unit in the first embodiment.

FIG. 4 is a cross-sectional view of the power generation unit in the first embodiment. As illustrated in FIG. 4, the power generation unit 20 includes an anode 41, an ion selective permeable membrane 42, a cathode 43, and a substrate 44. The anode 41, the ion selective permeable membrane 42, and the cathode 43 are disposed on the substrate 44. The ion selective permeable membrane 42 is interposed between the anode 41 and the cathode 43. The power generation unit 20 is a fuel cell using, for example, glucose and atmospheric air. The anode 41 is supplied with the tear 52 through the substrate 44, while the cathode 43 is supplied with atmospheric air or the like.

At the anode 41, the following glucose decomposition reaction is caused using a catalyst such as platinum.

$$C_6H_{12}O_6+2OH^-\rightarrow C_6H_{12}O_7+H_2O+2e^-$$

At the cathode 43, the following reaction is caused.

$$(\tfrac{1}{2})O_2+H_2O+2e^-\rightarrow 2OH^-$$

OH$^-$ generated in the cathode 43 moves to the anode 41 through the ion selective permeable membrane 42. Electromotive force (electric potential difference) is generated between the anode 41 and the cathode 43 by electrons e$^-$ generated at the anode 41 and electrons e$^-$ reacting at the cathode 43. The following reaction occurs as a whole.

$$C_6H_{12}O_6+(\tfrac{1}{2})O_2\rightarrow C_6H_{12}O_7$$

When the impedance of an external load connected between the anode 41 and the cathode 43 is constant, the electromotive force increases as the glucose concentration in the tear 52 increases. Thus, the power-supply voltage of the measuring circuit 22, the memory circuit 24, and the transmission circuit 26 increases as the glucose concentration increases. The power generation unit 20 may use other chemical reactions that generate electric power using sugars or biomolecules.

Figure 5:
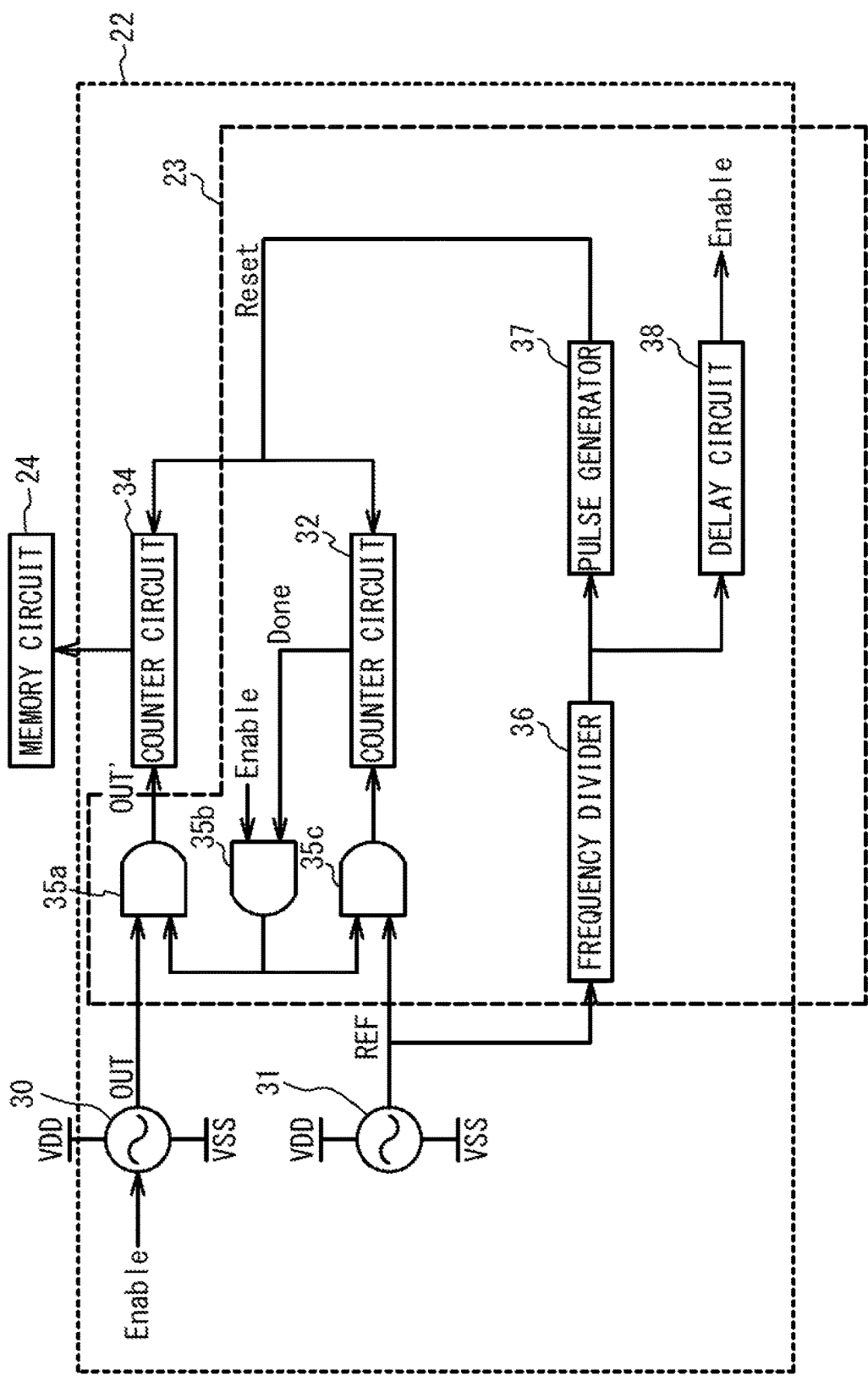
FIG. 5 is a circuit diagram of a measuring circuit in the first embodiment.

FIG. 5 is a circuit diagram of the measuring circuit in the first embodiment. The measuring circuit 22 includes oscillators 30 and 31, a timing circuit 23, and a counter circuit 34. When an Enable signal becomes high, the oscillator 30 outputs an oscillation signal OUT using the voltages VDD and VSS supplied from the power generation unit 20 as a power-supply voltage. The oscillator 31 outputs an oscillation signal REF using the voltages VDD and VSS as a power-supply voltage.

The timing circuit 23 generates a timing according to the oscillation signal REF. The timing circuit 23 includes a counter circuit 32, AND circuits 35a to 35c, a frequency divider 36, a pulse generator 37, and a delay circuit 38. The AND circuit 35c outputs the AND signal of the oscillation signal REF and the output of the AND circuit 35b to the counter circuit 32. When receiving a Reset signal from the pulse generator 37, the counter circuit 32 starts counting the number of pulses of the oscillation signal REF. The counter circuit 32 sets a Done signal at high level when the counting is started, and sets the Done signal at low level when the counting is completed. The AND circuit 35b outputs high level when the Done signal and the Enable signal are both high levels. The AND circuit 35a outputs the AND signal of the oscillation signal OUT and the output of the AND circuit 35b to the counter circuit 34.

The frequency divider 36 divides the oscillation signal REF, and outputs a signal with a period longer than that of the oscillation signal REF. The period of the signal output from the frequency divider 36 becomes the period at which the glucose concentration is measured. The pulse generator 37 generates a pulse when the signal output from the frequency divider 36 becomes high level, and outputs the generated pulse as the Reset signal. The counter circuits 32 and 34 are reset when receiving the Reset signal. The delay circuit 38 delays the signal output from the frequency divider 36. Therefore, the Reset signal and the Enable signal are output substantially simultaneously.

When the Done signal and the Enable signal are both high levels, the AND circuit 35a outputs the oscillation signal OUT to the counter circuit 34 as a signal OUT'. When the Done signal or the Enable signal is low level, the AND circuit 35a outputs low level. Therefore, the counter circuit 34 counts the number of pulses of the oscillation signal OUT during the period when the Done signal is high level. When the counting of the counter circuit 34 is completed, the memory circuit 24 stores each bit of the counter circuit 34.

Figure 6A:
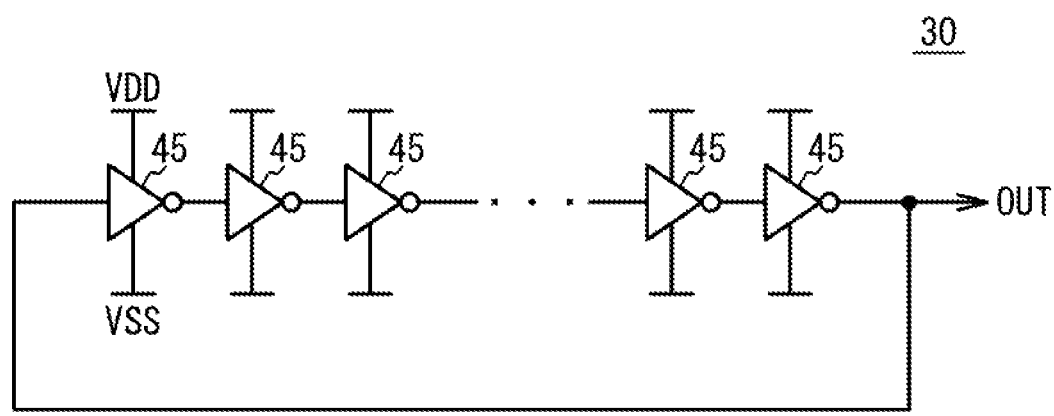
FIG. 6A and FIG. 6B are circuit diagrams of an oscillator in the first embodiment.
Figure 6B:
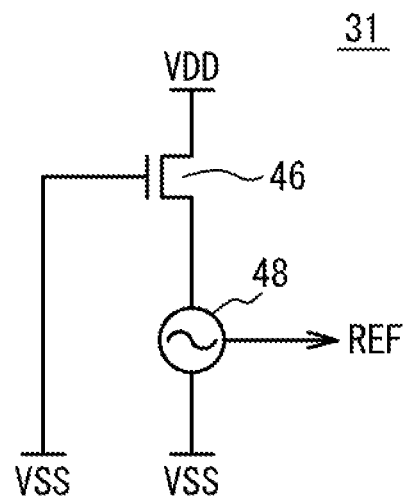

FIG. 6A and FIG. 6B are circuit diagrams of the oscillator in the first embodiment. As illustrated in FIG. 6A, the oscillator 30 is a ring oscillator. A plurality of inverter circuits 45 are connected in a ring shape. A period obtained by multiplying the delay time it takes for one inverter circuit 45 to be inverted by the number of the inverter circuits 45 is substantially equal to the period of the oscillation signal OUT. The power-supply voltage of the inverter circuit 45 is the electric potential difference between the voltages VDD and VSS. When the power-supply voltage decreases, the drive current for charging the inverter circuit 45 at the next stage decreases, and therefore the time it takes for the inverter circuit 45 to be inverted increases. Thus, as the power-supply voltage decreases, the period of the oscillation signal increases (i.e., the frequency becomes lower). The frequency of the oscillation signal OUT is preferably approximately 1 kHz to 100 kHz to reduce the l/f noise. That is, the period is preferably approximately 10 microseconds to 1 millisecond.

As illustrated in FIG. 6B, the oscillator 31 includes a field effect transistor (FET) 46 and an oscillator 48. The oscillator 48 is, for example, a ring oscillator. The source, the drain, and the gate of the FET 46 are respectively connected to the power supply of the oscillator 48, the power supply line to which the voltage VDD is supplied, and the ground line to which the voltage VSS is supplied. Thus, the FET 46 functions as a constant-current source. Since the supply-power current supplied to the oscillator 48 is constant, the period of the oscillation signal REF output from the oscillator 48 depends very little on the power-supply voltage. The period of the oscillation signal REF is preferably longer than the period of the oscillation signal OUT, and is preferably, for example, approximately 10 milliseconds to 1 second.

Figure 7:
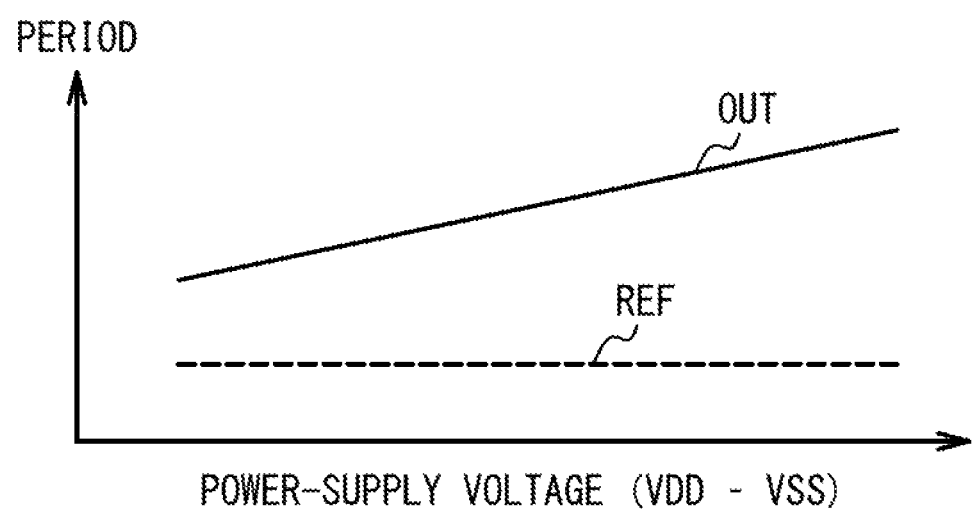
FIG. 7 is a schematic view illustrating the period of an oscillation signal with respect to a power-supply voltage in the first embodiment.

FIG. 7 is a schematic view illustrating the period of the oscillation with respect to the power-supply voltage in the first embodiment. As illustrated in FIG. 7, in the oscillator 30 illustrated in FIG. 6A, as the power-supply voltage increases, the period of the oscillation signal OUT becomes longer. In the oscillator 31 illustrated in FIG. 6B, the period of the oscillation signal REF depends very little on the power-supply voltage. The power-supply voltage dependence of the period of the oscillation signal REF output from the oscillator 31 (i.e., the amount of change in period/the amount of change in power-supply voltage) is preferably equal to or less than $1/5$ of, more preferably equal to or less than $1/10$ of, further preferably equal to or less than $1/20$ of the power-supply voltage dependence of the period, of the oscillation signal OUT output from the oscillator 30. The oscillators 30 and 31 may have circuit configurations other than those illustrated in FIG. 6A and FIG. 6B as long as the power-supply voltage dependence of the period of the oscillation signal REF is smaller than the power-supply voltage dependence of the period of the oscillation signal OUT.

Figure 8:
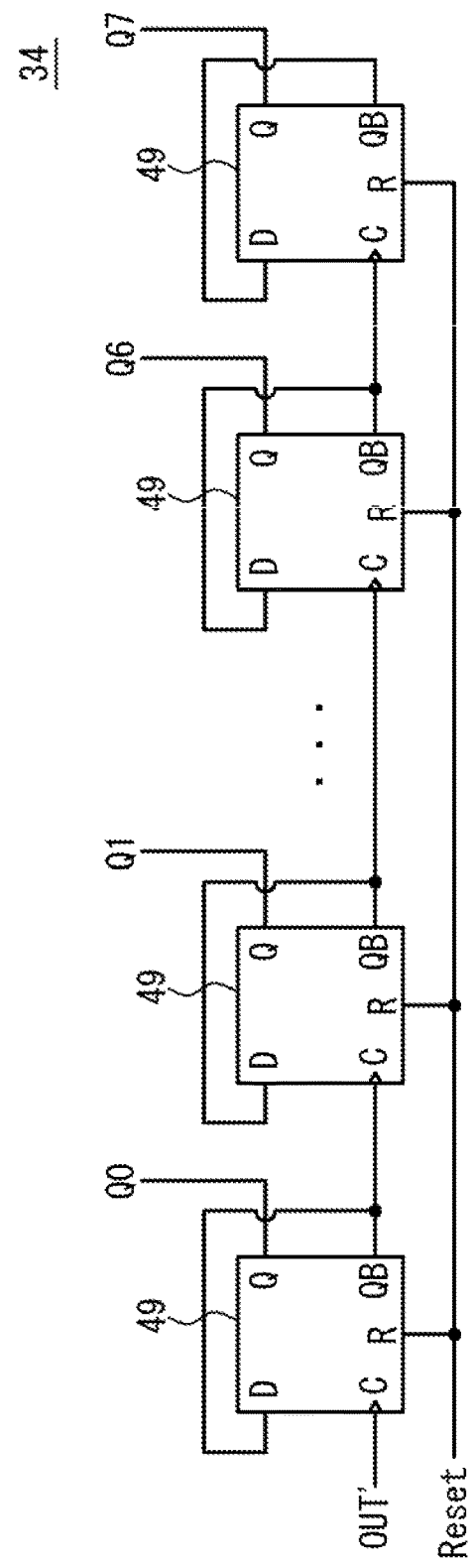
FIG. 8 is a circuit diagram of a counter circuit in the first embodiment.

FIG. 8 is a circuit diagram of the counter circuit in the first embodiment. An 8-bit counter circuit will be described as an example of the counter circuit 34. As illustrated in FIG. 8, the counter circuit 34 includes eight FFs 49 each being a D flip-flop. The signal OUT' output from the AND circuit 35a is input to the clock terminal C of the FF 49 at the first stage. The output terminal Q outputs bit data Q0. The output terminal QB (the complementary output terminal of the output terminal Q) is connected to the clock terminal C of the FF 49 at the next stage and the data terminal D of the FF 49 at the first stage. The Reset signal is input to the reset terminal R. The FFs 49 at the second and subsequent stages are connected in the same manner. The FFs 49 output bit data Q0 to data Q7, respectively. The same applies to the circuit of the counter circuit 32. The counter circuits 32 and 34 may be counter circuits that use FFs other than DFFs. The number of bits of the counter circuits 32 and 34 may be freely designed.

Figure 9A:
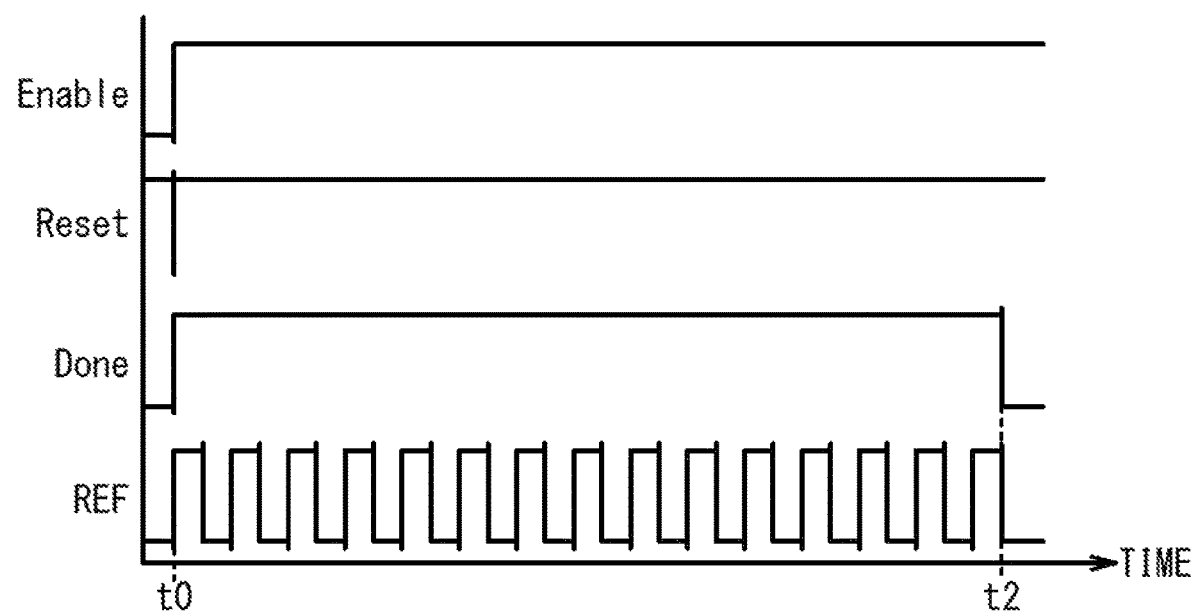
FIG. 9A and FIG. 9B illustrate signals of a timing circuit with respect to time in the first embodiment.
Figure 9B:
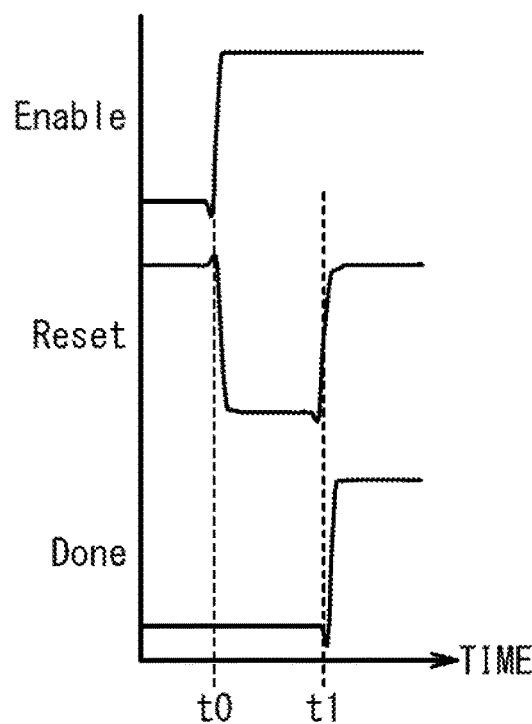

FIG. 9A and FIG. 9B illustrate signals of the timing circuit with respect to time in the first embodiment. FIG. 9B is an enlarged view of FIG. 9A. A 4-bit counter will be described as an example of the counter circuit 32. As illustrated in FIG. 9A, before time t0, the Enable signal is low level, the Reset signal is high level, and the Done signal is low level.

As illustrated in FIG. 9B, at time t0, the Enable signal becomes high level and the Reset signal becomes low level. When the Reset signal returns to high level at time t1, the counter circuits 32 and 34 reset, and start counting. The Done signal becomes high level. The interval between time t0 and time t1 is less than the period of the oscillation signal REF. In FIG. 9A, the Reset signal is illustrated so as to have no width at time t0. When the time scale is enlarged as illustrated in FIG. 9B, the Reset signal changes from high level to low level at time t0, and the Reset signal changes from low level to high level at time t1.

As illustrated in FIG. 9A, when counting 15 pulses of the oscillation signal REF, the counter circuit 32 becomes low level at time t2. As described above, the timing circuit 23 generates two timings corresponding to time t1 at which the Done signal becomes high level and time t2 at which the Done signal becomes low level according to the oscillation signal REF. Since the period of the oscillation signal REF is substantially constant regardless of the power-supply voltage, the interval between time t1 and time t2 is substantially constant regardless of the power-supply voltage.

Figure 10:
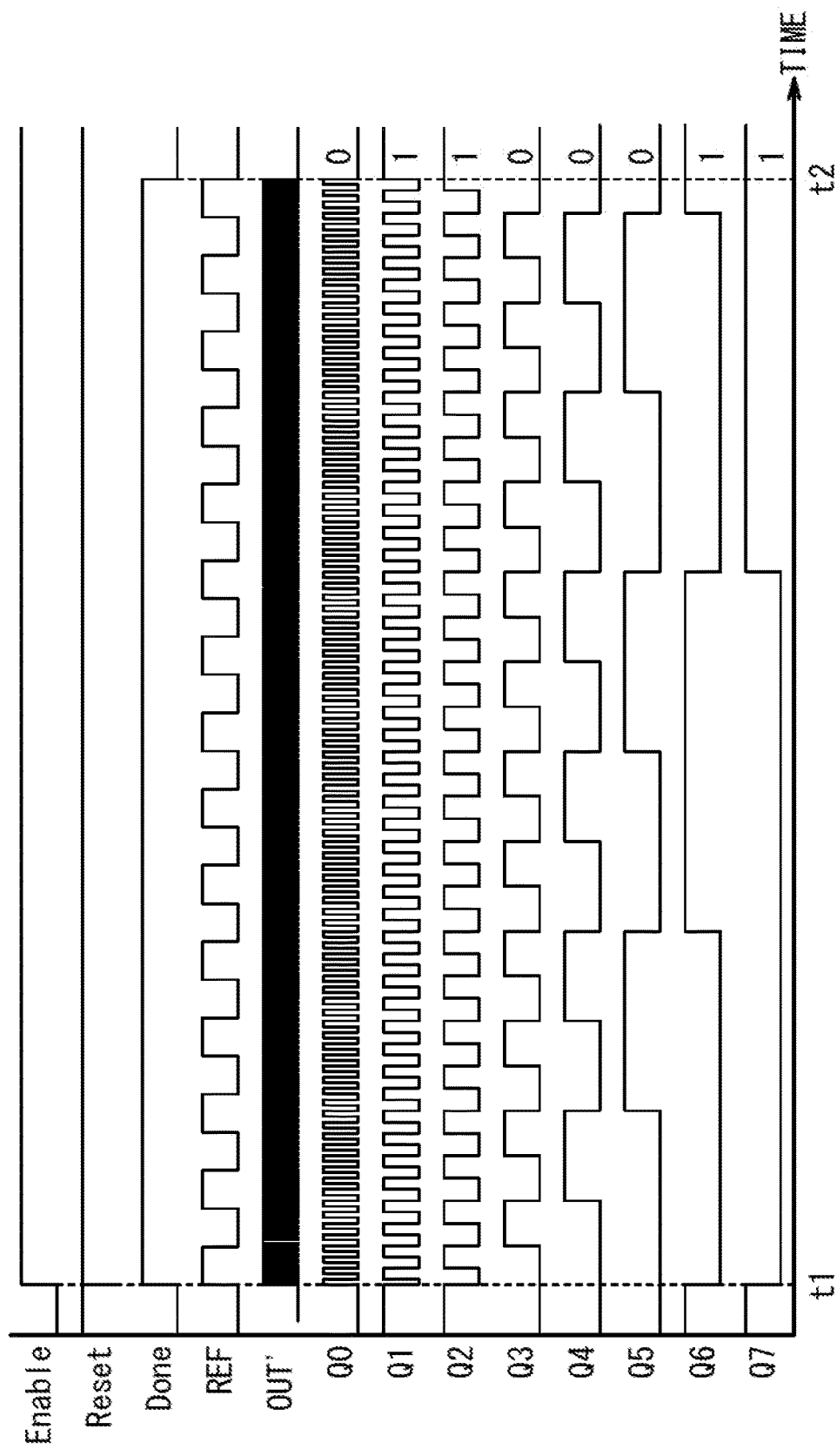
FIG. 10 illustrates signals of a counter circuit 34 with respect to time in the first embodiment.

FIG. 10 illustrates signals of the counter circuit 34 with respect to time in the first embodiment. The counter circuit 34 is an 8-bit counter. As illustrated in FIG. 10 the Enable signal, the Reset signal, the Done signal, and the oscillation signal REF are the same as those in FIG. 9A, respectively.

When the Done signal becomes high level at time t1, the oscillation signal OUT is input to the counter circuit 34 as the signal OUT'. The bit data Q0 of the 0th bit of the counter circuit 34 has a period that is two times the period of the oscillation signal OUT. The bit data Q1 of the 1st bit has a period that is four times the period of the oscillation signal OUT. The bit data Q7 of the 7th bit has a period that is 256 times the period of the oscillation signal OUT. At time t2 at which the Done signal becomes low level, the signal OUT' becomes low level. The FFs 49 of the counter circuit 34 hold the bit data Q0 to the bit date Q7 at time t2, respectively. In the example of FIG. 10, Q7 to Q0 become 11000110. The number obtained by deeming Q7 to Q0 to be a binary number is the number of pulses of the oscillation signal OUT between time t1 and time t2.

The period of the oscillation signal REF depends very little on the power-supply voltage as illustrated in FIG. 7. In addition, the timing circuit 23 uses digital circuits such as the counter circuit 32 and the AND circuits 35a to 35c. Therefore, even when the power-supply voltage fluctuates, the interval between time t1 and time t2 depends very little on the power-supply voltage and is substantially constant. As illustrated in FIG. 7, as the power-supply voltage becomes higher, the period of the oscillation signal OUT becomes longer. Therefore, as the power-supply voltage becomes higher (i.e., as the glucose concentration increases), the number of pulses of the oscillation signal OUT between time t1 and time t2 decreases. As the power-supply voltage becomes lower (i.e., the glucose concentration decreases), the number of pulses of the oscillation signal OUT between time t1 and time t2 increases. As described above, the measuring circuit 22 converts the glucose concentration into digital information indicating the number of pulses.

Figure 11:
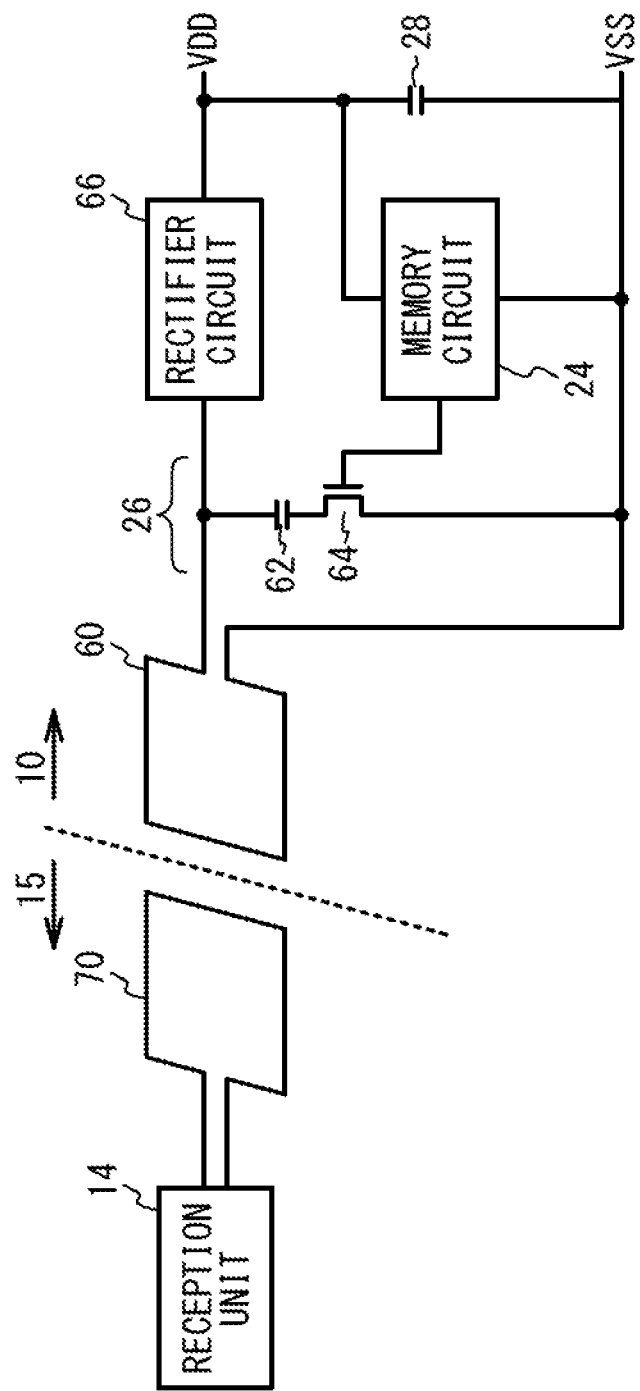
FIG. 11 is a circuit diagram of the periphery of a transmission circuit in the first embodiment.

FIG. 11 is a circuit diagram of the periphery of the transmission circuit in the first embodiment. As illustrated in FIG. 11, the measuring device 10 includes an antenna 60 and a rectifier circuit 66 in addition to the memory circuit 24, the transmission circuit 26, and the electricity storage device 28. The container device 15 includes an antenna 70 in addition to the reception unit 14.

The antenna 60 is a coil, a first end of the antenna 60 is connected to the transmission circuit 26, and a second end of the antenna 60 is connected to VSS. VSS is, for example, ground. The transmission circuit 26 includes a capacitor 62 and an FET 64. A first end of the capacitor 62 is connected to the second end of the antenna 60, while a second end of the capacitor 62 is connected to VSS through the FET 64. The gate of the FET 24 is connected to the memory circuit 24. The FET 24 is an N-channel FET. The second end of the antenna 60 is connected to the electricity storage device 28 through the rectifier circuit 66. The memory circuit 24 is supplied with electric power from the electricity storage device 28.

The container device 15 includes the antenna 70 in addition to the reception unit 14. The antenna 70 is, for example, a coil, and both ends of the antenna 70 are connected to the reception unit 14. When the contact lens 12 is stored in the container device 15, the antennas 60 and 70 are electromagnetically coupled. The reception unit 14 outputs an oscillation signal to the antenna 70. The induced current corresponding to the oscillation signal flows through the antenna 60. The rectifier circuit 66 rectifies the induced current. The rectified electric power is stored in the electricity storage device 28. The rectifier circuit 66 may be, for example, a half-wave rectifier circuit. When the power generation by the power generation unit 20 alone is sufficient to charge the electricity storage device 28, the rectifier circuit 66 does not have to be used to charge the electricity storage device 28.

When sufficient electric power is stored in the electricity storage device 28, the memory circuit 24 outputs Q7 to Q0 in sequence to the gate of the FET 64. For example, when Q7 is 1 (i.e., high level), the second end of the antenna 60 is connected to VSS through the capacitor 62. For example, when Q7 is 0 (i.e., low level), the capacitor 62 is not connected to VSS. Thus, the resonant frequency of the resonant circuit formed of the antenna 60 and the capacitor 62 when Q7 is 1 differs from the resonant frequency of the resonant circuit formed of the antenna 60 and the capacitor 62 when Q7 is 0. The antenna 70 is electromagnetically coupled to the antenna 60. Thus, when the resonant frequency of the resonant circuit formed of the antenna 60 and the capacitor 62 varies, the impedance of the antenna 70 varies. The reception unit 14 receives the bit of Q7 by detecting the variation in the impedance of the antenna 70. The reception unit 14 receives Q6 to Q0 in the same manner.

As a concrete example of the first embodiment, when the glucose concentration in the tear 52 is 20 mg/dL to 500 mg/dL, 8 bits are sufficient for the information about the glucose concentration. When the counter circuit 32 is a 4-bit counter circuit and the counter circuit 34 is an 8-bit counter circuit, the power consumption of the oscillators 30 and 31 and the timing circuit 23 is tens of nanowatts. When the memory circuit 24 stores 8-bit information every 5 minutes for 8 hours, the amount of data to be stored is 768 bits, and the storage capacity of the memory circuit 24 is 1 kbit. The power consumption of a 1-kbit SRAM is 7 nW. The power generation amount per unit area of the power generation unit 20 using glucose is approximately 30 nW/mm$^2$. Thus, the power generation of the power generation unit 20 can sufficiently cover the power consumption of the measuring circuit 22 and the memory circuit 24.

First Variation of the First Embodiment

Figure 12:
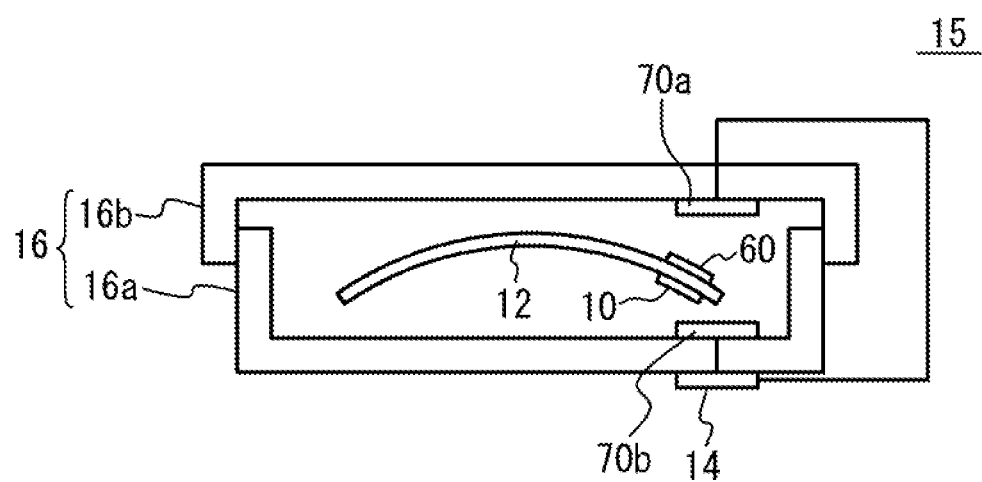
FIG. 12 is a cross-sectional view of a container device in a first variation of the first embodiment.

FIG. 12 is a cross-sectional view of a container device in accordance with a first variation of the first embodiment. As illustrated in FIG. 12, the contact lens 12 includes the antenna 60, and the container device 15 includes antennas 70a and 70b. When the contact lens 12 is stored in the container unit 16, the antennas 70a and 70b sandwich the antenna 60 therebetween. The remaining structure is the same as that in FIG. 1B.

Figure 13:
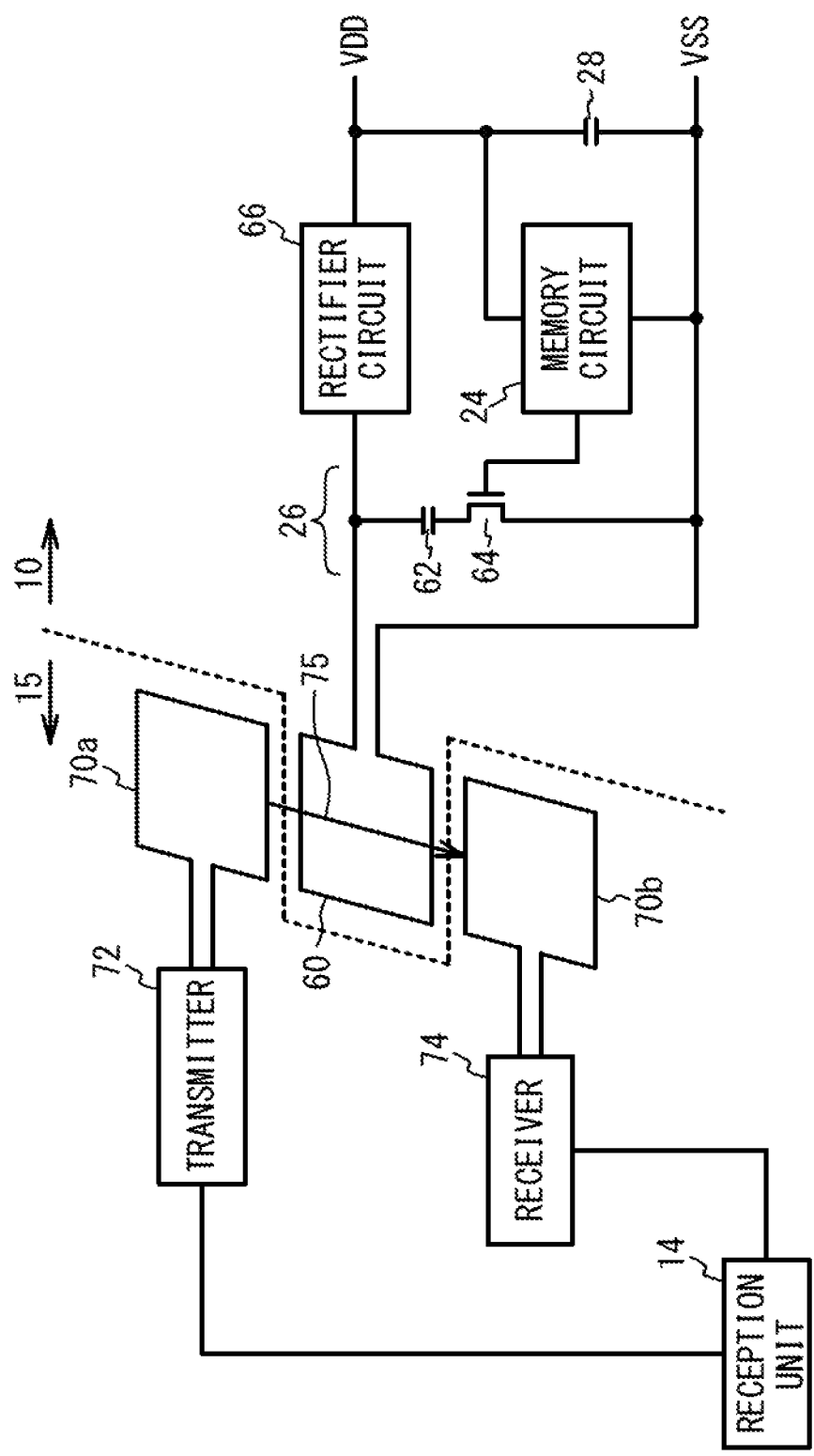
FIG. 13 is a circuit diagram of the periphery of the transmission circuit in the first variation of the first embodiment.

FIG. 13 is a circuit diagram of the periphery of the transmission circuit in the first variation of the first embodiment. As illustrated in FIG. 13, the container device 15 includes the antennas 70a and 70b, a transmitter 72, and a receiver 74. The antennas 70a and 70b are inductively coupled as indicated by an arrow 75. The transmitter 72 outputs an oscillation signal to the antenna 70a. The induced current having a frequency equal to that of the oscillation signal flows through the antenna 70b. The receiver 74 receives the induced current of the antenna 70b. The remaining structure is the same as that in FIG. 11.

When the memory circuit 24 outputs 0 to the gate of the FET 64, the resonant frequency of the antenna 60 does not vary. Therefore, the induced current flowing through the antenna 70b does not vary. When the memory circuit 24 outputs 1 to the gate of the FET 64, the resonant frequency of the resonant circuit of the antenna 60 and the capacitor 62 varies. This inhibits the electromagnetic coupling (the arrow 75) between the antennas 70a and 70b, and the induced current flowing through the antenna 70b decreases. The reception unit 14 can determine whether the output of the transmission circuit 26 is 0 or 1 on the basis of difference between the oscillation signal output from the transmitter 72 and the reception signal received by the receiver 74.

When the frequency of the oscillation signal output from the transmitter 72 is high, electromagnetic waves (the arrow 75) propagate from the antenna 70a to the antenna 70b. The resonant frequency of the resonant circuit of the antenna 60 and the capacitor 62 is adjusted to be approximately equal to the frequency of the electromagnetic wave. When the memory circuit 24 outputs 0, the antenna 60 does not reflect the electromagnetic wave. When the memory circuit 24 outputs 1, the electromagnetic wave is reflected by the antenna 60. This decreases the intensity of the electromagnetic wave received by the antenna 70b. The reception unit 14 can determine whether the output of the transmission circuit 26 is 0 or 1 on the basis of the difference between the intensity of the electromagnetic wave output from the transmitter 72 and the intensity of the electromagnetic wave received by the receiver 74.

For example, as disclosed in 2011 Symposium on VLSI Circuits Digest of Technical Paper pp. 162-163, the reception unit 14 may determine whether the output of the transmission circuit 26 is 0 or 1 on the basis of the bit error rate of the digital signal transmitted from the transmitter 72 to the receiver 74. Alternatively, the transmitter 72 transmits a clock signal and the receiver 74 receives the clock signal. The reception unit 14 may determine whether the output of the transmission circuit 26 is 0 or 1 on the basis of the change in the duty ratio of the transmitted clock signal and the received clock signal. The change in the duty ratio may be detected using a time to digital convertor (TDC) or the like.

The antenna 60 only inhibits the electromagnetic coupling between the antennas 70a and 70b or the propagation of the electromagnetic wave. Thus, the power consumption of the transmission circuit 26 is reduced.

The measuring device disclosed in Patent Document 1 uses electric power generated using the decomposition reaction of biomolecules, and thus does not need to be supplied with the source power from the outside. However, the measuring device mounted to the contact lens transmits the information about the blood glucose level in real time. Since the transmission circuit transmits the information within a range of at least approximately 1 meter, the power generation amount of the power generation unit may be insufficient.

In the first embodiment and the variation thereof, the measuring device 10 is mounted to the contact lens 12, and stores information about the amount of electric power generated using sugars in the tear 52. That is, the power generation unit 20 of the measuring device 10 generates electric power using sugars in the tear 52, and the memory circuit 24 (a storage unit) of the measuring device 10 stores the power generation amount of the power generation unit 20. The container device 15 stores the contact lens 12, and receives the information about the power generation amount stored in the measuring device 10 using the near-field wireless communication method when the contact lens 12 is stored. That is, when the contact lens is stored in the container unit 16, the transmission circuit 26 (a transmission unit) of the measuring device 10 transmits the information about the power generation amount stored in the memory circuit 24 to the container device 15 using the near-field wireless communication method. The reception unit 14 of the container device 15 receives the information about the power generation amount stored in the measuring device 10 using the near-field wireless communication method.

As described above, the measuring device 10 does not have to have the transmission circuit that transmits the information about the power generation amount in real time like Patent Document 1 because the measuring device 10 stores the information about the power generation amount while the contact lens 12 is attached to the eye of the user. When the contact lens 12 is stored in the container device 15, the information about the power generation amount is transmitted from the measuring device 10 to the container device 15 using the near-field wireless communication method. The power consumption of the near-field communication method is small, and therefore the power consumption of the measuring device 10 is reduced. In addition, in the near-field wireless communication method, as illustrated in FIG. 11, the electric power for transmitting the information from the container device 15 to the measuring device 10 can be supplied.

The measuring device 10 generates and stores the information about the power generation amount using, as a power supply, the electric power generated using sugars in the tear 52. As described above, the electric power generated by the power generation unit 20 can cover the electric power for the measuring circuit 22 and the memory circuit 24.

As in the first variation of the first embodiment, the container device 15 includes the antenna 70a (a first antenna) and the antenna 70b (a second antenna). The measuring device 10 includes the antenna 60 (a third antenna) to be sandwiched between the antennas 70a and 70b when the measuring device 10 is stored in the container device 15. The transmission circuit 26 transmits the information to the reception unit 14 by the antenna 60 inhibiting the electromagnetic coupling between the antennas 70a and 70b or the propagation of the electromagnetic wave.

The antennas 70a and 70b can easily sandwich the antenna 60 therebetween by storing the contact lens 12 in the container unit 16. In addition, the power consumption of the transmission circuit 26 can be reduced.

In the measuring device 10, the power generation unit 20 generates the electromotive force through the reaction of sugars. The oscillator 30 (a first oscillator) uses the electromotive force of the power generation unit 20 as a power-supply voltage and generates the oscillation signal OUT (a first oscillation signal) of which the period varies in response to the variation in electromotive force. For example, as the electromotive force increases, the period decreases. The oscillator 31 (a second oscillator) uses the electromotive force as a power-supply voltage and generates the oscillation signal REF (a second oscillation signal) of which the variation in period with respect to the variation in the electromotive force is smaller than that of the oscillator 30. The timing circuit 23 uses the electromotive force as a power-supply voltage and generates a first timing indicating time t1 and a second timing indicating time t2 on the basis of the oscillation signal REF. The counter circuit 34 uses the electromotive force as a power-supply voltage and counts the number of pulses of the oscillation signal OUT between the first timing and the second timing. The measuring device 10 may generate the electromotive force through the decomposition reaction of biomolecules instead of the decomposition reaction of sugars in the tear 52.

Accordingly, the electromotive force that is the analog value can be converted into the number of pulses that is the digital value using the small electric power and low voltage generated by the power generation unit 20. Therefore, the power consumption of the measuring device 10 is further reduced.

The memory circuit 24 stores the information about the number of pulses as the information about the power generation amount. Thus, the memory circuit 24 is able to store the number of pulses that is the digital value representing the electromotive force.

The transmission circuit 26 transmits the information on the number of pulses stored in the memory circuit 24 using the near-field wireless communication method. This reduces the power consumption for transmitting the information.

The electricity storage device 28 accumulates the electric power generated by the power generation unit 20, and supplies the electric power to the memory circuit 24 to retain the information about the number of pulses stored in the memory circuit 24 when the power generation unit 20 does not generate electric power. This allows the memory circuit 24 to retain the information while the contact lens 12 is stored in the container device 15 and the information is transmitted to the container device 15 even when the memory circuit 24 is a volatile memory.

The first embodiment and the variation thereof describe an exemplary case where the measuring device 10 mounted to the contact lens generates electric power using sugars in the tear 52. At least, the measuring device 10 is attached to a living body such as a human body. The liquid used by the measuring device 10 to generate electric power may be body fluids such as blood or cutaneous intercellular fluid in the body of the living body, or bodily secretions such as saliva, sweat, or urine secreted by the living body. For example, the measuring device 10 may be mounted to an article that is to be in direct contact with the body surface of the living body, such as a ring, a piercing jewelry, or earrings, and the measuring device 10 may generate electric power using sugars in sweat. The container unit 16 of the container device 15 stores the measuring device to be attached to the living body.

SECOND EMBODIMENT

Figure 14A:
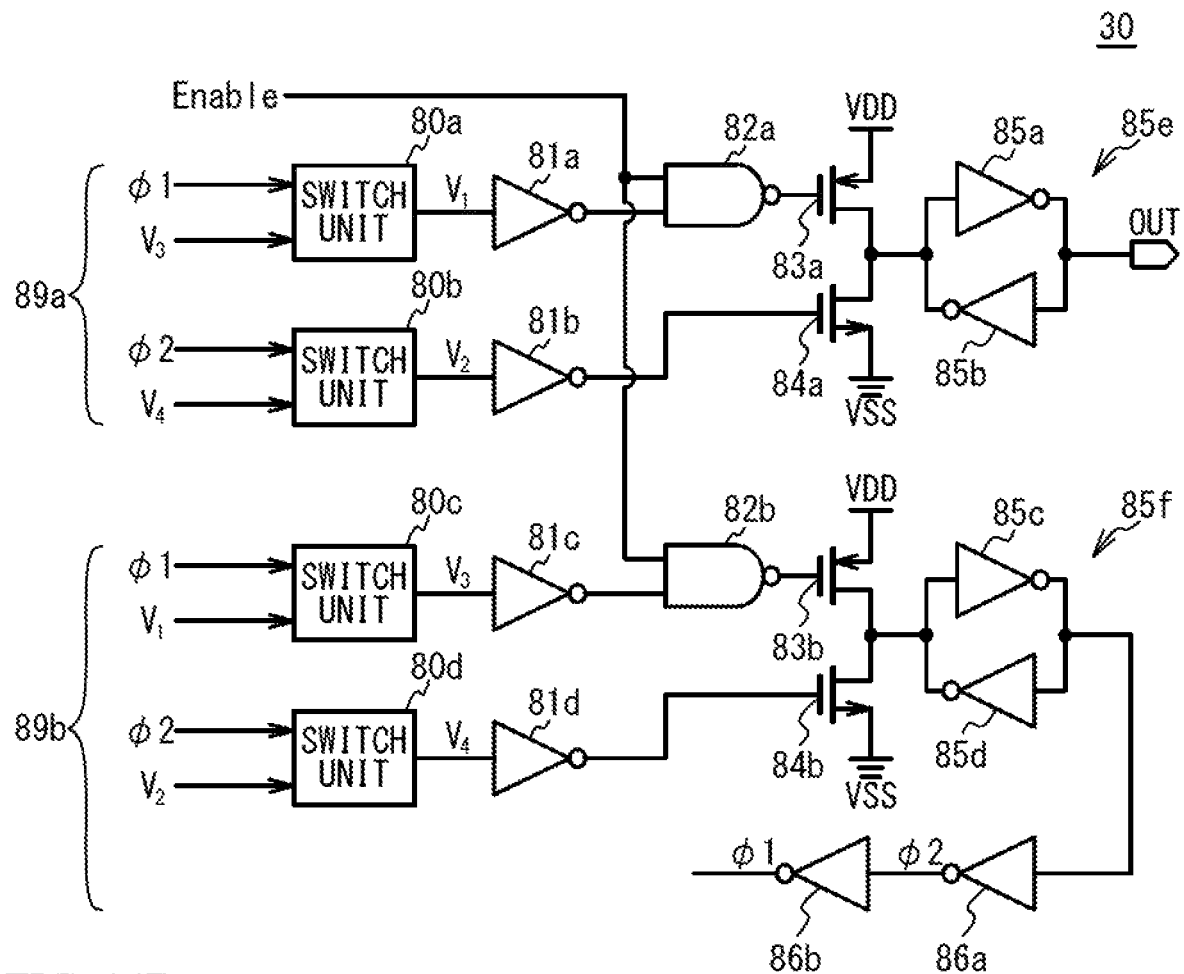
FIG. 14A is a circuit diagram of an oscillator 30 in a second embodiment.
Figure 14B:
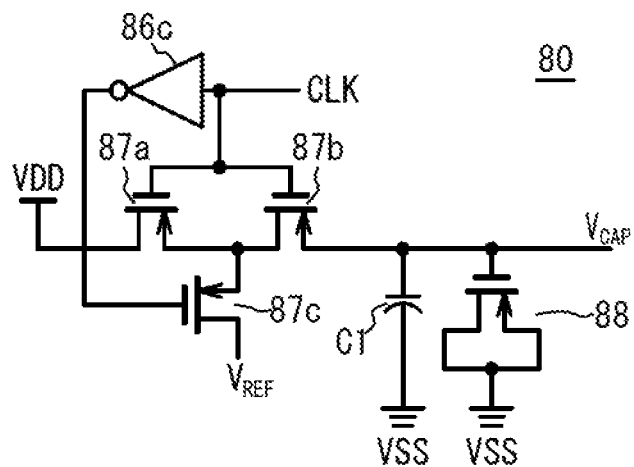
FIG. 14B is a circuit diagram of a switch unit.

As a second embodiment, a measuring circuit illustrated in FIG. 5 was fabricated using the 65 nm complementary), metal oxide semiconductor (CMOS) technology. FIG. 14A is a circuit diagram of the oscillator 30 in the second embodiment and FIG. 14B is a circuit diagram of a switch unit. The oscillator 30 is a circuit based on the method disclosed in IEEE J. Solid State Circuits, Vol. 51, no. 6, pp. 1423-1435.2016.

As illustrated in FIG. 14A in the oscillator 30, signals Φ1 and $V_3$ are input to a switch unit 80a, signals Φ2 and $V_4$ are input to a switch unit 80b, signals Φ1 and $V_1$ are input to a switch unit 80c, and signals Φ2 and $V_2$ are input to a switch unit 80d. The switch units 80a to 80d output the signals $V_1$ to $V_4$ to inverters 81a to 81d respectively.

The Enable signal and the output signal of the inverter 81a are input to a NAND circuit 82a. A P type field effect transistor (PFET) 83a and an N type field effect transistor (NFET) 84a are connected in series between the power supply supplied with the voltage VDD and the ground supplied with the voltage VSS. The output signal of the NAND circuit 82a is input to the gate of the PFET 83a and the output signal of the inverter 81b is input to the gate of the NFET 84a. The node to which the drains of the PFET 83a and the NFET 84a are connected is connected to the node of a latch 85e in which inverters 85a and 85b are circularly connected. The other node of the latch 85e is connected to the output terminal that outputs the oscillation signal OUT.

The Enable signal and the output signal of the inverter 81c are input to a NAND circuit 82b. A PFET 83b and an NFET 84b are connected in series between VDD and VSS. The output signal of the NAND circuit 82b is input to the PFET 83b, and the output signal of the inverter 81d is input to the gate of the NFET 84b. The node to which the drains of the PFET 83b and the NFET 84b are connected to the node of a latch 85f in which inverters 85c and 85d are circularly connected. The other node of the latch 85f is connected to an inverter 86a. The inverter 86a outputs the signal Φ2, and an inverter 86b outputs the signal Φ1 obtained by inverting the signal Φ2.

As illustrated in FIG. 14B in a switch unit 80 (corresponding to the switch units 80a to 80d FIG. 14A) a signal CLK is input to the gates of PFETs 87a and 87b connected between VDD and $V_{CAP}$. An inverter 86c inverts the signal CLK, and outputs the resulting signal to the gate of a PFET 87c. The PFET 87c connects the node between the PFETs 87a and 87b with the terminal supplied with a signal $V_{REF}$. A capacitor C1 and a metal oxide semiconductor (MOS) capacitor 88 are connected in parallel between the source of the PFET 87b (the node of $V_{CAP}$ and VSS. The MOS capacitor 88 is connected in the forward direction.

In the switch unit 80a, the signals CLK, $V_{REF}$, and $V_{CAP}$ in FIG. 14B correspond to the signals Φ1, $V_3$, and $V_1$ in FIG. 14A, respectively. In the switch unit 80b, the signals CLK, $V_{REF}$, and $V_{CAP}$ correspond to the signals Φ2, $V_4$, and $V_2$, respectively. In the switch unit 80c, the signals CLK, $V_{REF}$, and $V_{CAP}$ correspond to the signals Φ1, and $V_3$, respectively. In the switch unit 80d, the signals CLK, $V_{REF}$, and $V_{CAP}$ correspond to the signals Φ2, $V_2$, and VD, respectively.

In the oscillator 30, the electric charges of the capacitor C1 and the MOS capacitor 88 in the switch unit 80 are discharged as the gate leak current of the MOS capacitor 88. The oscillating frequency is determined by the time it takes for $V_{CAP}$ to reach the threshold voltage of the inverter 86c from the power-supply voltage VDD-VSS. The PFETs 87a to 87c and the inverter 86c in the switch unit 80 construct a switch circuit having a small leak current. Thus, the discharge from the capacitor C1 is mostly due to the gate leak current of the MOS capacitor 88. A low-leakage switch circuit including the PFETs 87a to 87c and the inverter 86c is a circuit based on IEEE Int. Symp. Circuits Syst., pp. 557-560, 2006.

The period T that is the inverse of the oscillating frequency of the oscillator 30 is expressed in the following equation (1) where the equivalent resistance value of the MOS capacitor 88 is represented by $R_{MOS}$, the total capacitance value of the capacitor C1 and the MOS capacitor 88 connected to the nodes of $V_{CAP}$ is represented by $C_{OSCH}$.

$$T=2\times R_{MOS}\times C_{OSCH}\times \ln(2) \tag{1}$$

Here, ln indicates natural logarithm.

The equivalent resistance value $R_{MOS}$ of the forward gate leak current of the MOS capacitor 88 depends on the voltage applied to the gate of the MOS capacitor 88. For example, $R_{MOS}$ is inversely proportional to the voltage applied to the gate. Therefore, as the power-supply voltage VDD-VSS increases, $R_{MOS}$ decreases and the period T becomes shorter. That is, the oscillating frequency becomes higher. As described above, the oscillating frequency of the oscillator 30 largely depends on the power-supply voltage VDD-VSS.

The oscillator 30 includes blocks 89a and 89b. The block 89a includes the switch units 80a and 80b, the inverters 81a and 81b, the NAND circuit 82a, the PFET 83a, the NFET 84a, and the latch 85e. The block 89b includes the switch units 80c and 80d, the inverters 81c, 81d, 86a, and 86b, the NAND circuit 82b, the PFET 83b, the NFET 84b, and the latch 85f. The block 89b generates the signals Φ1 and Φ2, while the block 89a generates the oscillation signal OUT.

Figure 15:
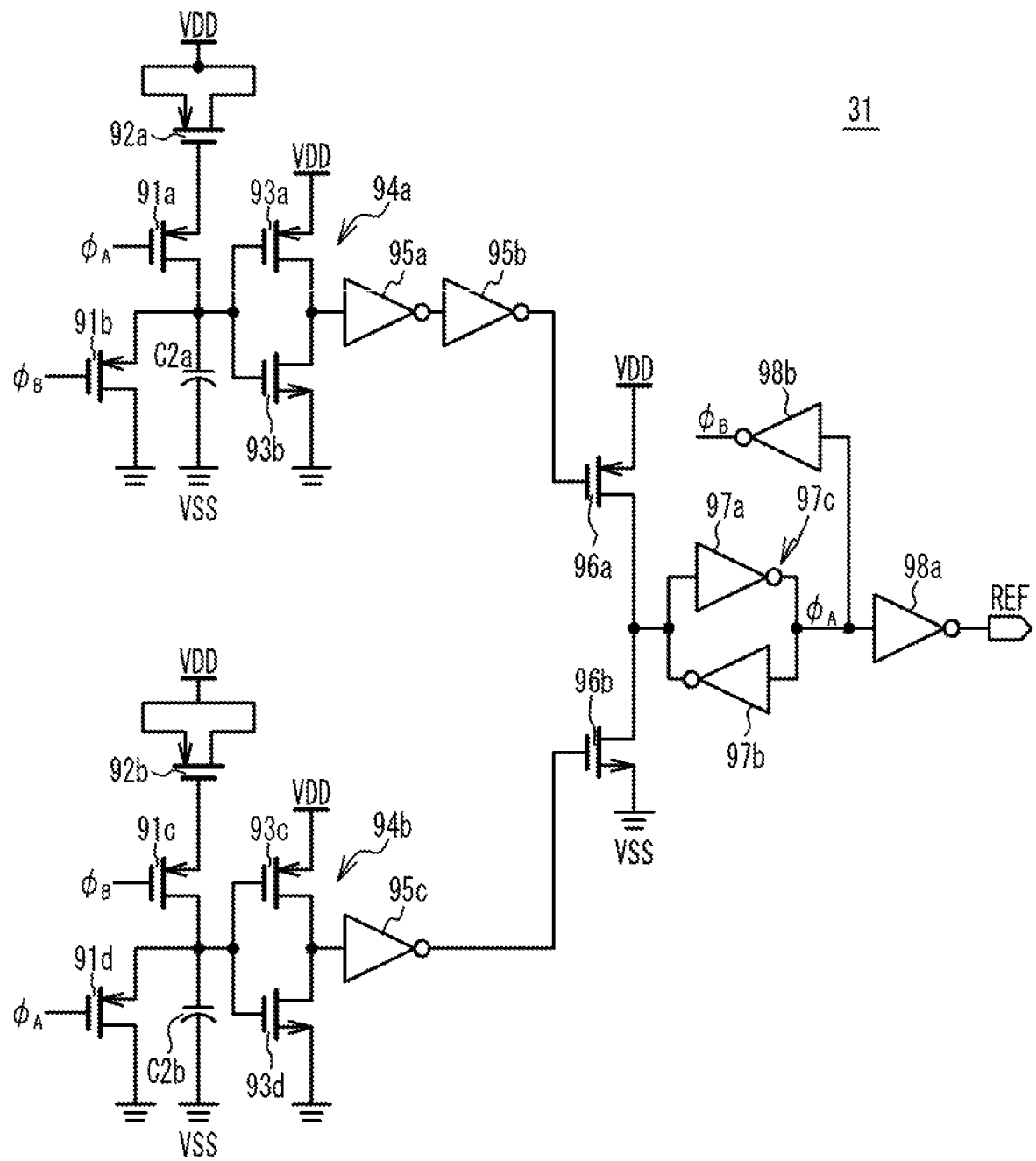
FIG. 15 is a circuit diagram of an oscillator 31 in the second embodiment.

FIG. 15 is a circuit diagram of the oscillator 31 in the second embodiment. The oscillator 31 is a circuit based on the method disclosed in IEEE J. Solid State Circuits, Vol. 51, no. 6, pp. 1331-1346, 2016.

As illustrated in FIG. 15, in the oscillator 31, a MOS capacitor 92a and PFETs 91a and 91b are connected in series between the power supply supplied with the voltage VDD and the ground supplied with the voltage VSS. The MOS capacitor 92a is connected in the backward direction. The capacitor C2a is connected in parallel to the PFET 91b. A signal $\Phi_A$ is input to the gate of the PFET 91a, and a signal $\Phi_B$ is input to the gate of the PFET 91b. The signal of the node between the PFETs 91a and 91b is input to an inverter 94a having a PFET 93a and an NFET 93b. The output signal of the inverter 94a is input to the gate of a PFET 96a through inverters 95a and 95b.

A MOS capacitor 92b and PFETs 91c and 91d are connected in series between VDD and VSS. The signal $\Phi_B$ is input to the gate of the PFET 91c, and the signal $\Phi_A$ is input to the gate of the PFET 91d. A capacitor C2b is connected in parallel to the PFET 91d. The signal of the node between the PFETs 91c and 91d is input to an inverter 94b having a PFET 93c and an NFET 93d. The output signal of the inverter 94b is input to the gate of an NFET 96b through an inverter 95c.

The PFET 96a and the NFET 96b are connected in series between VDD and VSS. The node to which the drains of the PFET 96a and the NFET 96b are connected is connected to the node of a latch 97c in which inverters 97a and 97b are circularly connected. The other node of the latch 97c outputs the signal $\Phi_A$. An inverter 98a inverts the signal $\Phi_A$, and outputs the resulting signal to the output terminal that outputs the oscillation signal REF. An inverter 98b inverts the signal $\Phi_A$, and outputs the signal DB.

In the oscillator 31, the MOS capacitor 92a is used as a current source for charging the capacitor C2a, and the MOS capacitor 92b is used as a current source for charging the capacitor C2b. The oscillating frequency f of the oscillator 31 is expressed in the following equation (2) where the gate leak current values of the MOS capacitors 92a and 92b are represented by $I_{gate}$, the capacitance values of the capacitors C2a and C2b are represented by $C_{OSCL}$, and the threshold voltages of the inverters 94a and 94b are represented by $V_{INV}$.

$$F = I_{gate}/(2 \times C_{OSCL} \times V_{INV}) \quad (2)$$

The threshold voltages $V_{INV}$ of the inverters 94a and 94b are proportional to the power-supply voltage VDD-VSS. The backward gate leak currents of the MOS capacitors 92a and 92b are proportional to the power-supply voltage VDD-VSS. Therefore, the oscillating frequency f depends very little on the power-supply voltage.

The number of stages (the number of bits) of the counter circuit 32 was set at four stages, and the number of stages of the counter circuit 34 was set at eight stages. The aera of the oscillator 30 was 0.0027 mm$^2$, the area of the oscillator 31 was 0.0005 mm$^2$, and the area of the measuring circuit 22 was 0.0047 mm$^2$.

Figure 16A:
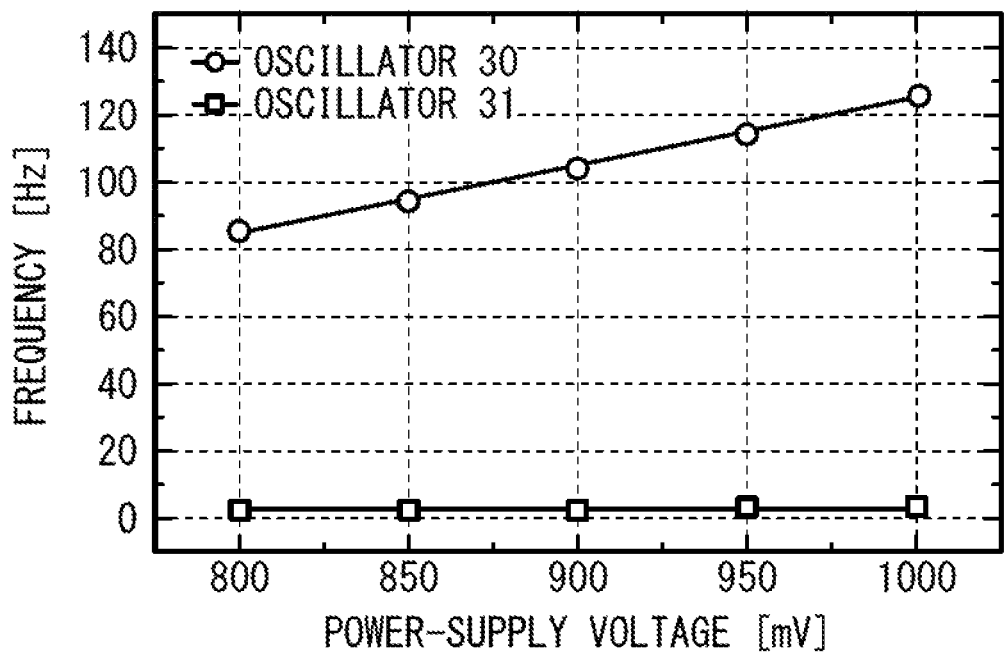
FIG. 16A is a graph of an oscillating frequency versus a power-supply voltage in the second embodiment.

FIG. 16A is a graph of the oscillating frequency versus the power-supply voltage in the second embodiment. Dots indicate measurement points, and lines connect the dots. As presented in FIG. 16A, when the power-supply voltage (VDD-VSS) is varied within a range from 800 mV to 1000 mV, the oscillating frequency of the oscillator 30 varies within a range from 85.8 Hz to 126.2 Hz. The oscillating frequency of the oscillator 31 varies within a range from 1.9 Hz to 3.2 Hz. The sensitivity of the oscillating frequency of the oscillator 30 to the power-supply voltage is 202 mHz/mV, and the sensitivity of the oscillating frequency of the oscillator 31 to the power-supply voltage is 6.6 mHz/mV. As seen above, the oscillating frequency of the oscillator 30 largely varies with the power-supply voltage, while the oscillating frequency of the oscillator 31 varies very little with the power-supply voltage.

Figure 16B:
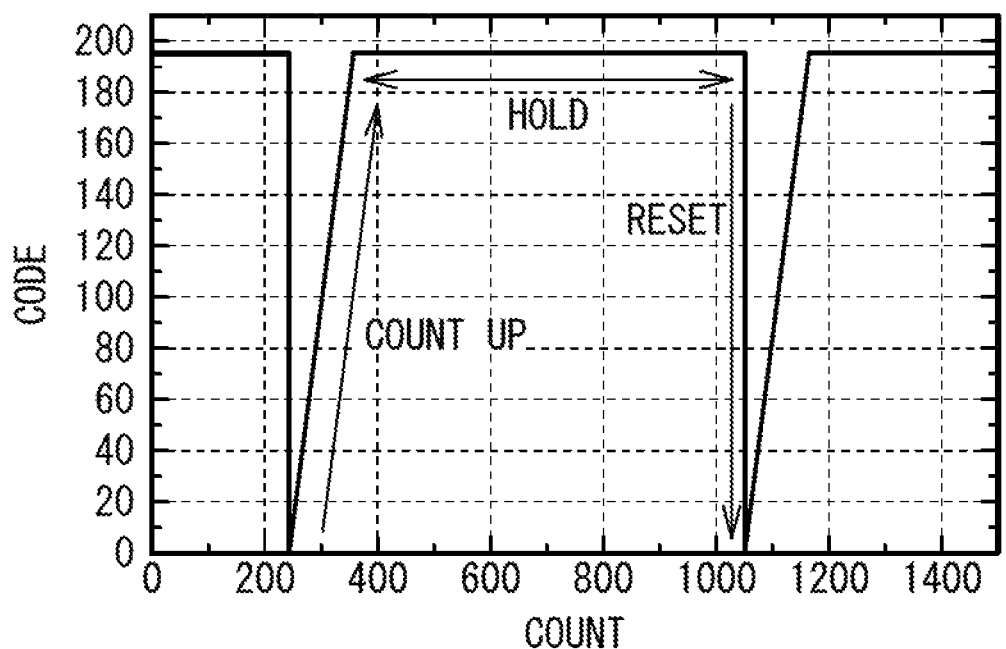
FIG. 16B is a graph of a code versus a count.

FIG. 16B is a graph of a code versus a count in the second embodiment. The power-supply voltage was set at 900 mV. The count corresponds to the number of pulses of the oscillation signal OUT of the oscillator 30, and the code is the number expressing the outputs Q7 to Q0 of the counter circuit 34 as a decimal. When the Enable signal becomes high level, the counter circuit 34 counts the number of pulses of the oscillation signal OUT, and the code increases (i.e., count up). When the counting is completed, the counter circuit 34 retains (i.e., holds) the code corresponding to the power-supply voltage of 900 mV. When the Reset signal becomes high level, the counter circuit 34 is reset, and the code becomes 0. As seen above, the counter circuit 34 operates properly.

Figure 17A:
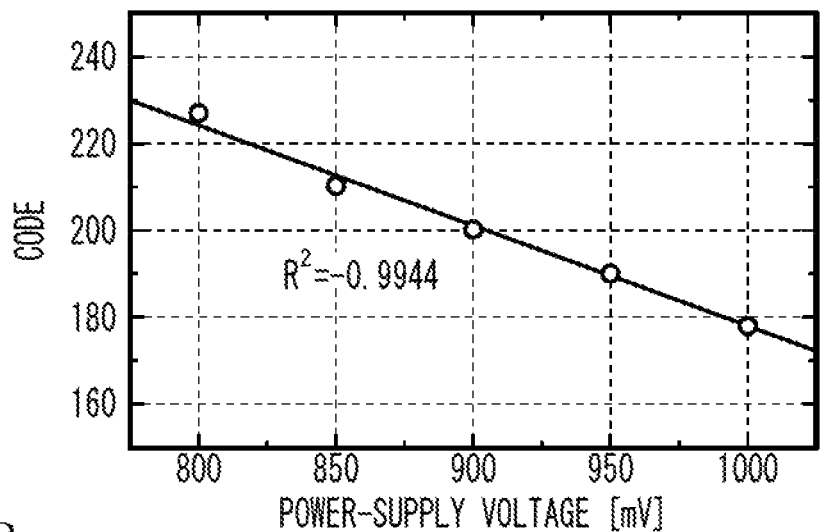
FIG. 17A is a graph of a code versus a power-supply voltage in the second embodiment.

FIG. 17A is a graph of a code versus power-supply voltage in the second embodiment. Dots represent measurement points, and a line is an approximate line. As illustrated in FIG. 17A, when the power-supply voltage is varied from 800 mV to 1000 mV, the code varies. The determination coefficient R$^2$ is −0.9944, and the relationship between the power-supply voltage and the code is substantially approximated by a straight line.

Figure 17B:
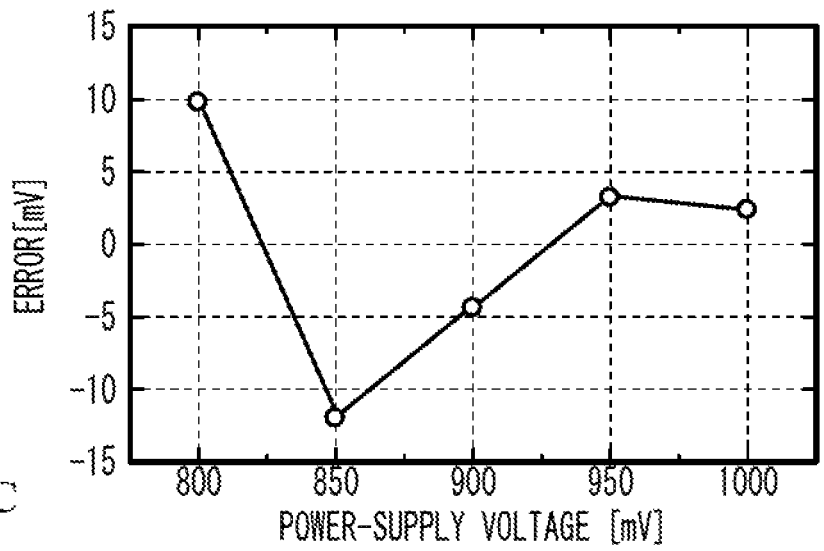
FIG. 17B is a graph of an error versus a power-supply voltage.

FIG. 17B is a graph of an error versus power-supply voltage in the second embodiment. The error is the difference between the measurement point and the approximate curve in FIG. 17A. As illustrated in FIG. 17B, the largest value of the error in the power-supply voltage due to use of the code is +10 mV, and the smallest value of the error in the power-supply voltage due to use of the code is −12 mV. As illustrated in FIG. 17A and FIG. 17B, the measuring circuit 22 can convert the power-supply voltage into the code.

Figure 17C:
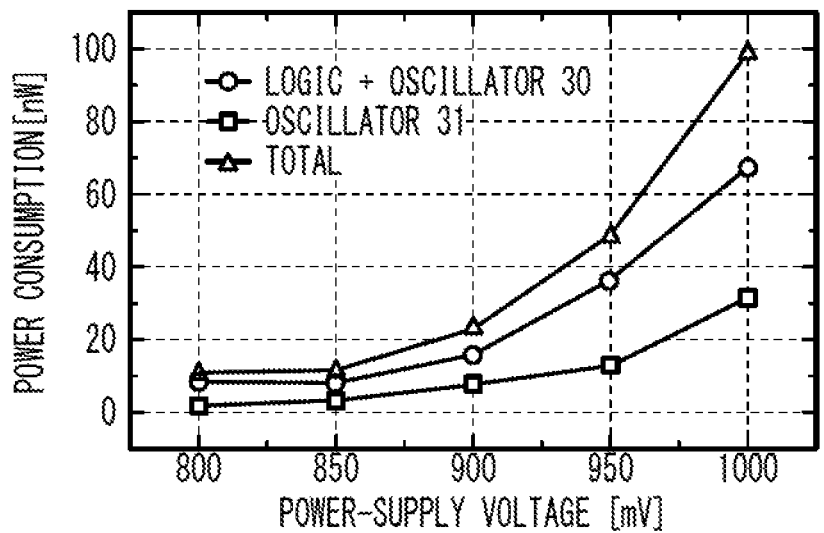
FIG. 17C is a graph of power consumption versus power-supply voltage.

FIG. 17C is a graph of power consumption versus power-supply voltage in the second embodiment. Circular dots indicate the total power consumption of the logic circuit and the oscillator 30, rectangular dots indicate the power consumption of the oscillator 31, and rhombic dots indicate the total power consumption of the measuring circuit 22. As illustrated in FIG. 17C, when the power-supply voltage is 800 mV, the power consumption is approximately 11 nW, and when the power-supply voltage is 1000 mV, the power consumption is approximately 100 nW. As seen above, the power consumption of the measuring circuit 22 is reduced.

In the second embodiment, the frequency of the oscillation signal REF output from the oscillator 31 is set in a sub-Hz range, and the frequency of the oscillation signal OUT output from the oscillator 30 is set to be dozens of times the frequency of the oscillation signal REF. Thus, the reduction in switching power and a high sampling rate (i.e., high resolution of the power-supply voltage) are both achieved. As seen above, the measuring circuit 22 of the second embodiment is able to convert the power-supply voltage into the code with less power consumption. Further small power-supply voltage can be converted into the code with small power consumption by improving the circuit of the measuring circuit 22. The oscillator other than that of the second embodiment may be used for the oscillators 30 and 31 of the first embodiment.

THIRD EMBODIMENT

A third embodiment is an exemplary case where the solar cell supplies electric power to the transmission circuit, and the transmission circuit transmits the information about the electromotive force of the power generation unit while the contact lens is attached to the eye of the user.

Figure 18:
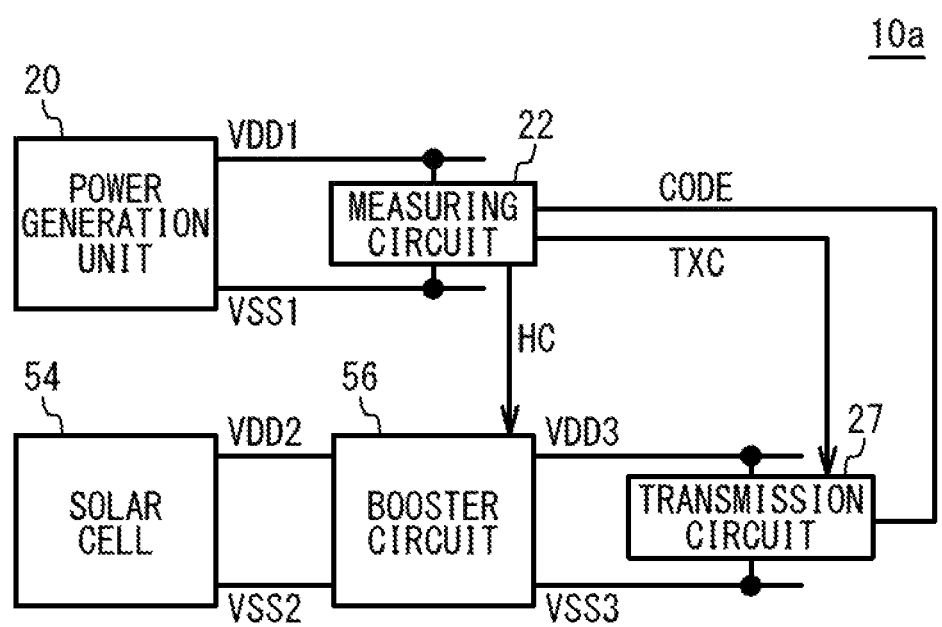
FIG. 18 is a block diagram of a measuring device in accordance with third embodiment.

FIG. 18 is a block diagram of a measuring device in accordance with the third embodiment. As illustrated in FIG. 18, a measuring device 10a includes the power generation unit 20, the measuring circuit 22, a transmission circuit 27, a solar cell 54, and a booster circuit 56. The power generation unit 20 supplies the electromotive force to the measuring circuit 22 as a power-supply voltage (voltage VDD1-voltage VSS1). The solar cell 54 converts the light emitted to the contact lens 12 into the electric power. The electromotive force of the solar cell 54 is a voltage VDD2-VSS2. The booster circuit 56 boosts the voltage VDD2-VSS2 to the voltage VDD3-VSS3. The booster circuit 56 supplies the boosted electric power to the transmission circuit 27. The electric power for the measuring circuit 22 is not supplied from the solar cell 54. The electric power for the transmission circuit 27 is not supplied from the power generation unit 20.

The measuring circuit 22 converts the electromotive force of the power generation unit 20 into the code, and outputs the code to the transmission circuit 27. The code is formed of the bits output from the counter circuit 34 in FIG. 5. The measuring circuit 22 outputs a control signal TXC to the transmission circuit 27, and outputs a control signal HC to the booster circuit 56.

Figure 19A:
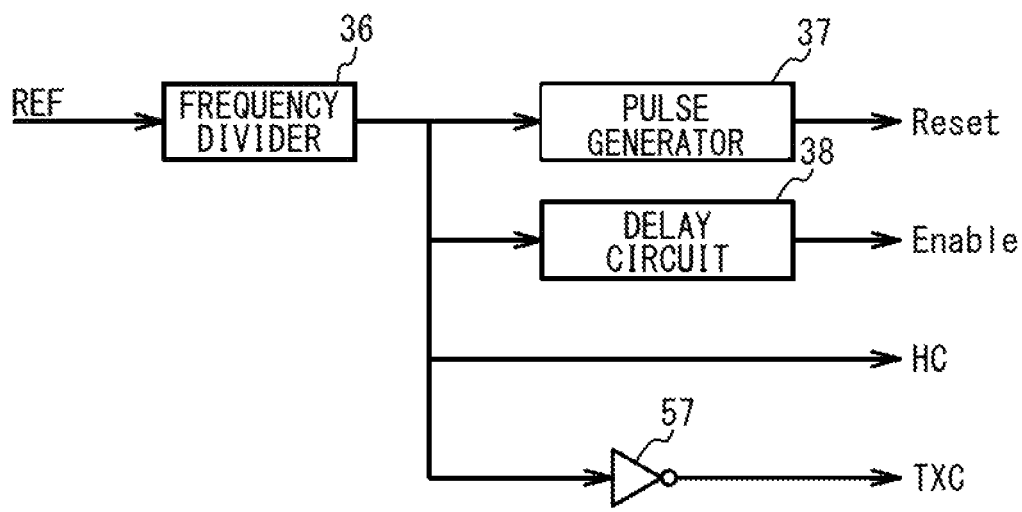
FIG. 19A is circuit diagram of a circuit that generates control signals in third embodiment.
Figure 19B:
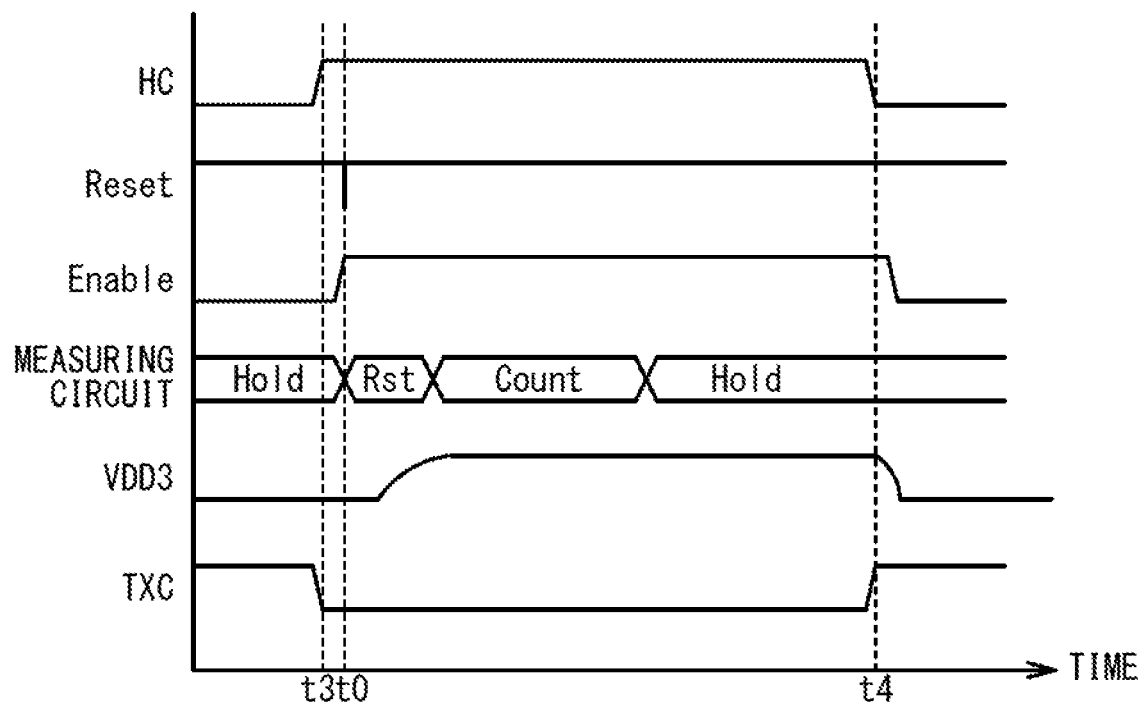
FIG. 19B illustrates control signals with respect to time.

FIG. 19A is a circuit diagram of a circuit generating control signals in the third embodiment, and FIG. 19B illustrates control signals with respect to time. As illustrated in FIG. 19A, the output of the frequency divider 36 of the measuring circuit 22 in FIG. 5 becomes the control signal HC, and the output of the frequency divider 36 becomes the control signal TXC through an inverter 57. The remaining circuits of the measuring circuit 22 are the same as those in FIG. 5.

As illustrated in FIG. 19B when the output of the frequency divider 36 is low level, the control signal HC holds low level, the Reset signal holds high level, the Enable signal holds low level, and the measuring circuit 22 holds a digital code corresponding to the electromotive force of the power generation unit 20 (Hold). The output voltage VDD3 of the booster circuit 56 is 0 V, and the control signal TXC is high level, When the output of the frequency divider 36 becomes high level at time t3, the control signal HC becomes high level. At slightly delayed time to, a pulse is output as the Reset signal, and the Enable signal becomes high level. This resets the measuring circuit 22 (Rst). Thereafter, the counter circuit 34 of the measuring circuit 22 counts the number of pulses corresponding to the electromotive force of the power generation unit 20, and generates the code (Count). Thereafter, the measuring circuit 22 holds the code (Hold).

When the control signal HC becomes high level, the booster circuit 56 is activated, and starts boosting the output voltage of the solar cell 54. The boosted electric power is stored in an electricity storage device such as a capacitor (for example, a capacitor C56 in FIG. 20). Therefore, VDD3 increases from 0 V, and becomes a voltage sufficient for the operation of the transmission circuit 27.

When the output of the frequency divider 36 becomes low level at time t4, the control signal HC becomes low level and the control signal TXC becomes high level. After a short delay, the Enable signal becomes low level. When the control signal TXC becomes high level, the transmission circuit 27 is activated, and transmits the code that has been held. This causes the electric charge accumulated in the electricity storage device to be discharged, and VDD3 returns to 0 V.

Figure 20:
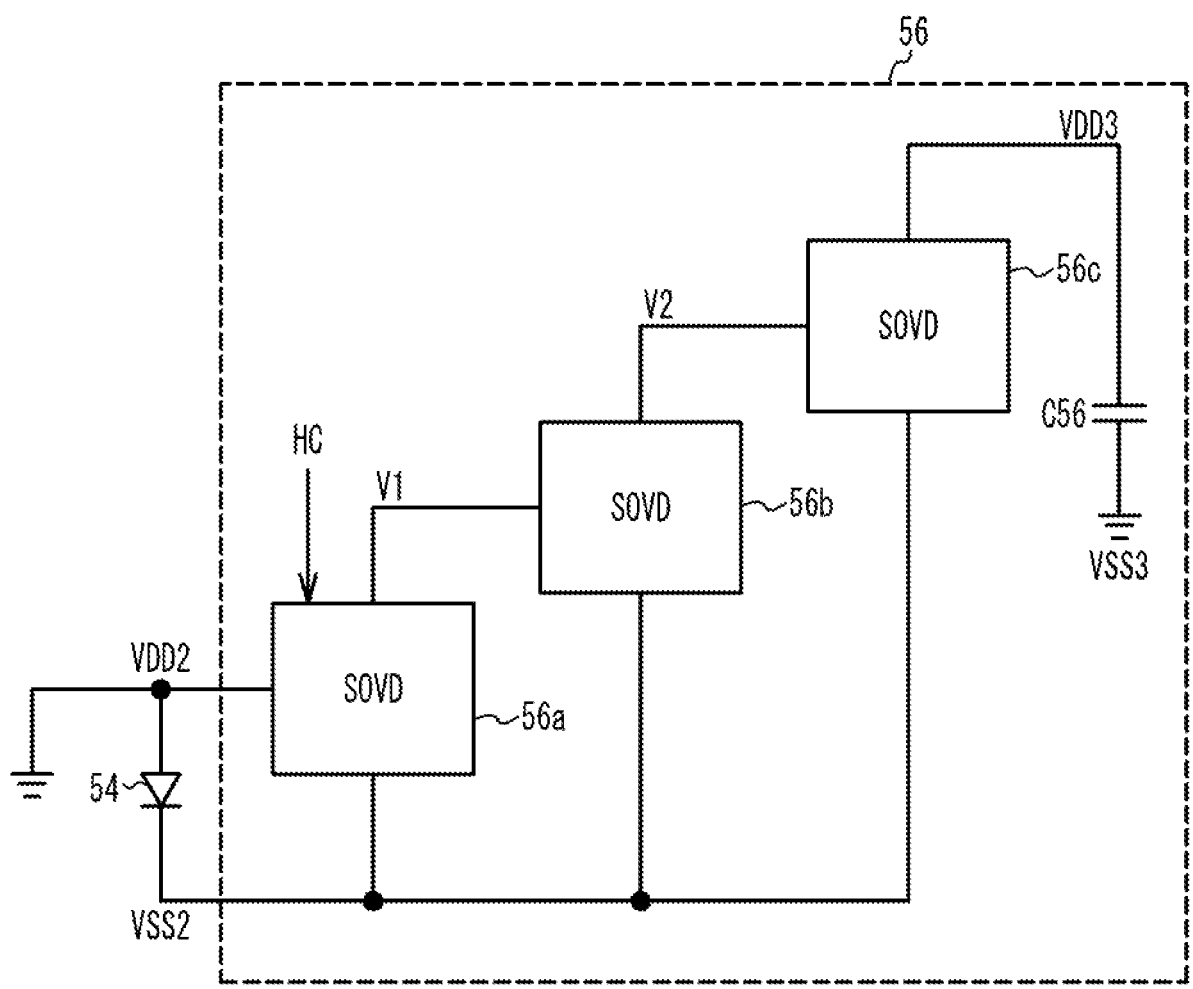
FIG. 20 is a circuit diagram of a booster circuit in the third embodiment.

FIG. 20 is a circuit diagram of the booster circuit in the third embodiment. The booster circuit 56 includes self-oscillating voltage doublers (SOVD) 56a to 56c that form three stages. The output voltage of the solar cell 54 is VDD2-VSS2. The SOVD 56a boosts VDD2-VSS2 to V1-VSS2. The SOVD 56a is activated by the control signal HC. The SOVD 56b boosts V1-VSS2 to V2-VSS2. The SOVD 56c boosts V2-VSS2 to VDD3-VSS2. The capacitor C56 is connected to the output of the SOVD 56c. The voltage VDD3-VSS3 obtained by boosting the electromotive force of the solar cell 54 is applied to the capacitor C56, and the electric charge is accumulated in the capacitor C56.

Figure 21:
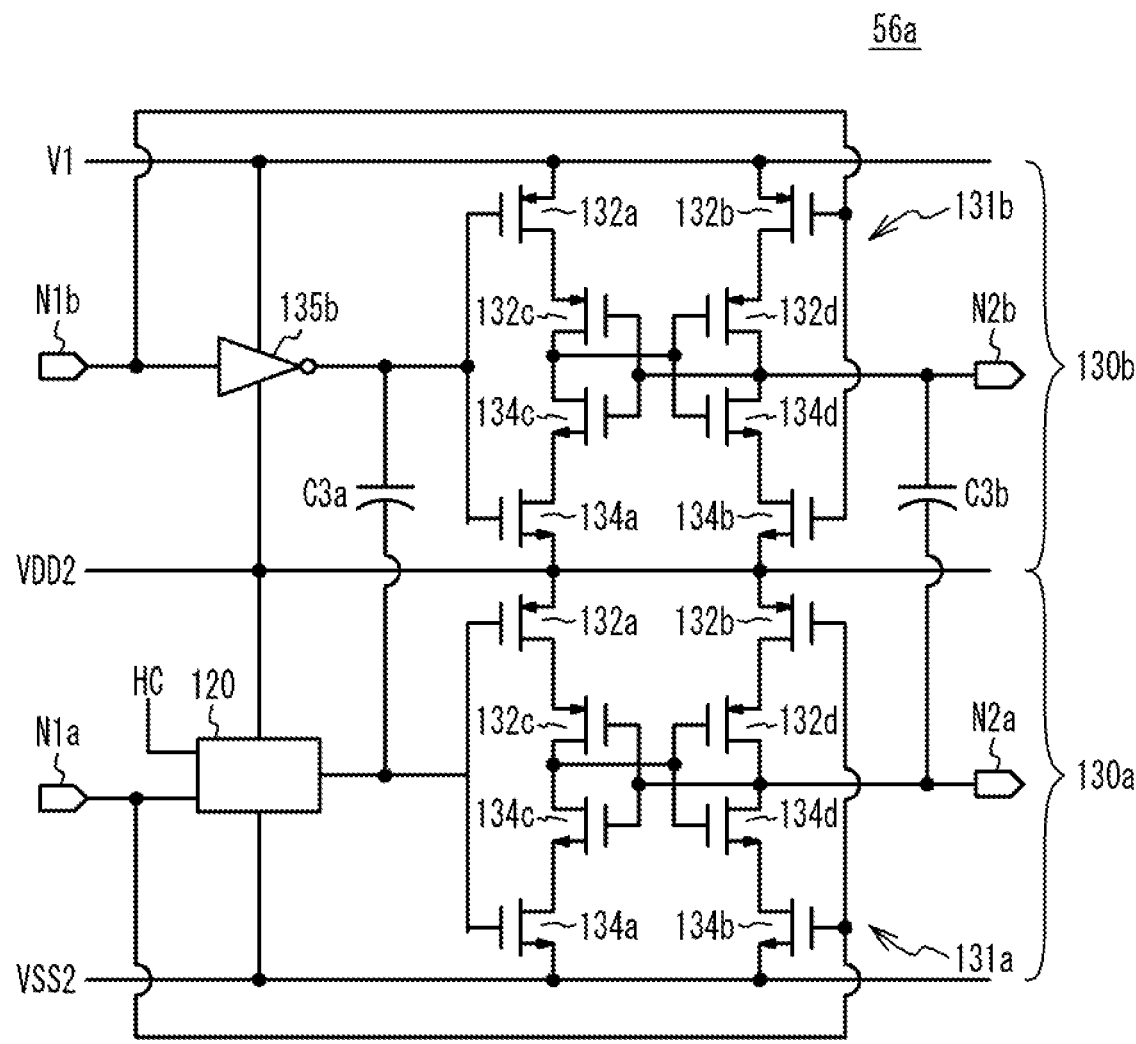
FIG. 21 is a circuit diagram of an SOVD in the third embodiment.

FIG. 21 is a circuit diagram of the SOVD in the third embodiment. In the SOVD 56a, a starting inverter circuit 120 and a delay circuit 131a are connected between a power supply line to which VDD2 is supplied and a power supply line to which VSS2 is supplied. An inverter circuit 135b and a delay circuit 131b are connected between a power supply line to which V1 is supplied and a power supply line to which VDD2 is supplied. Each of the delay circuits 131a and 131b includes PFETs 132a to 132d and NFETs 134a to 134d.

The output of the starting inverter circuit 120 is connected to the gates of the PFET 132a and the NFET 134a of the delay circuit 131a. The drains of the PFET 132d and the NFET 134d of the delay circuit 131a are connected to a node N2a. The gates of the PFET 132b and the NFET 134b of the delay circuit 131a are connected to an input node N1a of the starting inverter circuit 120. A capacitor C3a is connected between the output of the starting inverter circuit 120 and the output of the inverter circuit 135b. A capacitor C3b is connected between the output of the delay circuit 131a and the output of the delay circuit 131b.

When the control signal HC is high level, the starting inverter circuit 120 inverts the signal of the node N1a, and outputs the resulting signal. The delay circuit 131a delays the output of the starting inverter circuit 120, and outputs the delayed output to the input of the starting inverter circuit 120. Thus, the starting inverter circuit 120 and the delay circuit 131a form a ring oscillator.

The output of the inverter circuit 135b is connected to the gates of the PFET 132a and the NFET 134a of the delay circuit 131b. The gates of the PFET 132b and the NFET 134b of the delay circuit 131b are connected to an input node N1b of the inverter circuit 135b. Thus, the inverter circuit 135b and the delay circuit 131a form a ring oscillator. The node N2a is connected to the node N1b. A node N2b is connected to the node N1a of the SOVD 56b at the next stage.

When the control signal HC is input to the starting inverter circuit 120, the starting inverter circuit 120 and the delay circuit 131a oscillate. When the starting inverter circuit 120 and the delay circuit 131a oscillate, the inverter circuit 135b and the delay circuit 131b oscillate, and VDD2-VSS2 is boosted to V1-VDD2.

Figure 22:
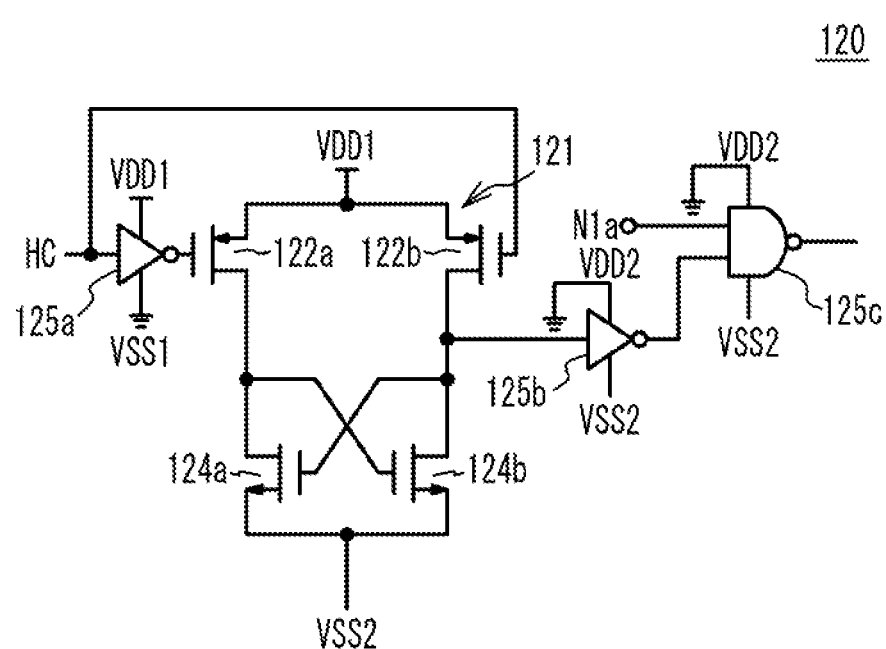
FIG. 22 is a circuit diagram of a starting inverter circuit in the third embodiment.

FIG. 22 is a circuit diagram of the starting inverter circuit in the third embodiment. The starting inverter circuit 120 includes inverters 125a and 125b, a circuit 121, and a NAND circuit 125c. The power-supply voltage of the inverter 125a is VDD1-VSS1, the power-supply voltage of the circuit 121 is VDD1-VSS2, and the power-supply voltage of the inverter 125b and the NAND circuit 125c is VDD2-VSS2.

The circuit 121 includes PFETs 122a and 122b and NFETs 124a and 124b. When the control signal HC becomes high level, the gate of the PFET 122a becomes low level, and the gate of the PFET 122b becomes high level. The gate of the NFET 124a becomes low level, and the gate of the NFET 124b becomes high level. Thus, the output of the circuit 121 becomes low level. The output of the inverter 125b becomes high level. When the control signal HC is low level, the NAND circuit 125c outputs high level regardless of the level of the node N1a, and when the control signal HC is high level, the NAND circuit 125c inverts the level of the node N1a and outputs the inverted level. Thus, when the control signal HC becomes high level while the node N1a is low level, the starting inverter circuit 120 outputs high level. Thus, the starting inverter circuit 120 and the delay circuit 131a in FIG. 21 oscillate, and the SOVD 56a is activated. Thereafter, while the control signal HC is high level, the NAND circuit 125c functions as an inverter circuit.

Figure 23:
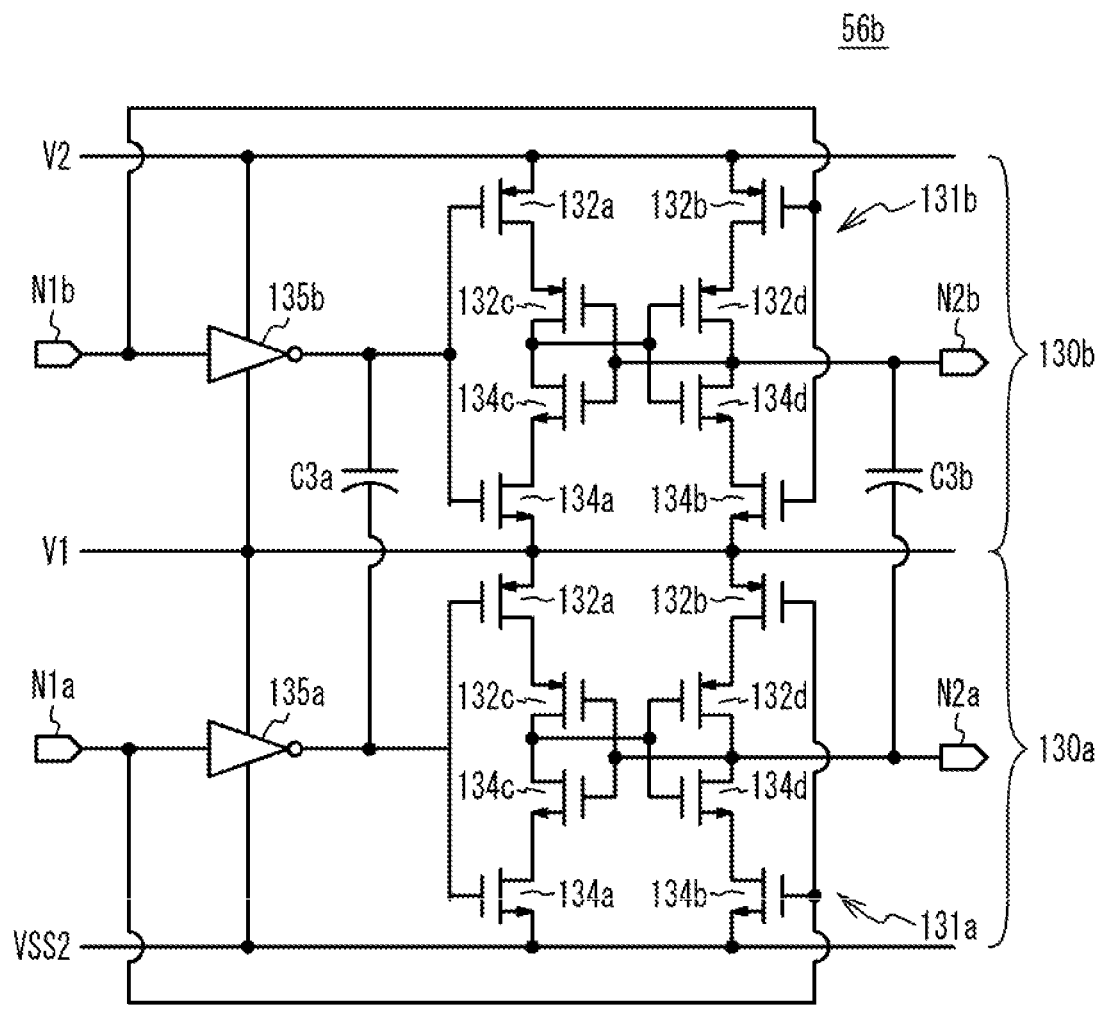
FIG. 23 is a circuit diagram of another SOVD in the third embodiment.

FIG. 23 is a circuit diagram of the SOVD in the third embodiment. In the SOVD 56b, an inverter circuit 135a and the delay circuit 131a are connected between a power supply line to which V1 is supplied and a power supply line to which VSS2 is supplied. The inverter circuit 135b and the delay circuit 131b are connected between a power supply line to which V2 is supplied and a power supply line to which V1 is supplied. The SOVD 56b boosts V1-VSS2 to V2-VSS2. Other structures are the same as those of the SOVD 56a, and the description thereof is thus omitted. The SOVD 56c boosts V2-VSS2 to VDD3-VSS2. Other structures are the same as those of the SOVD 56b, and the description thereof is thus omitted.

Figure 24:
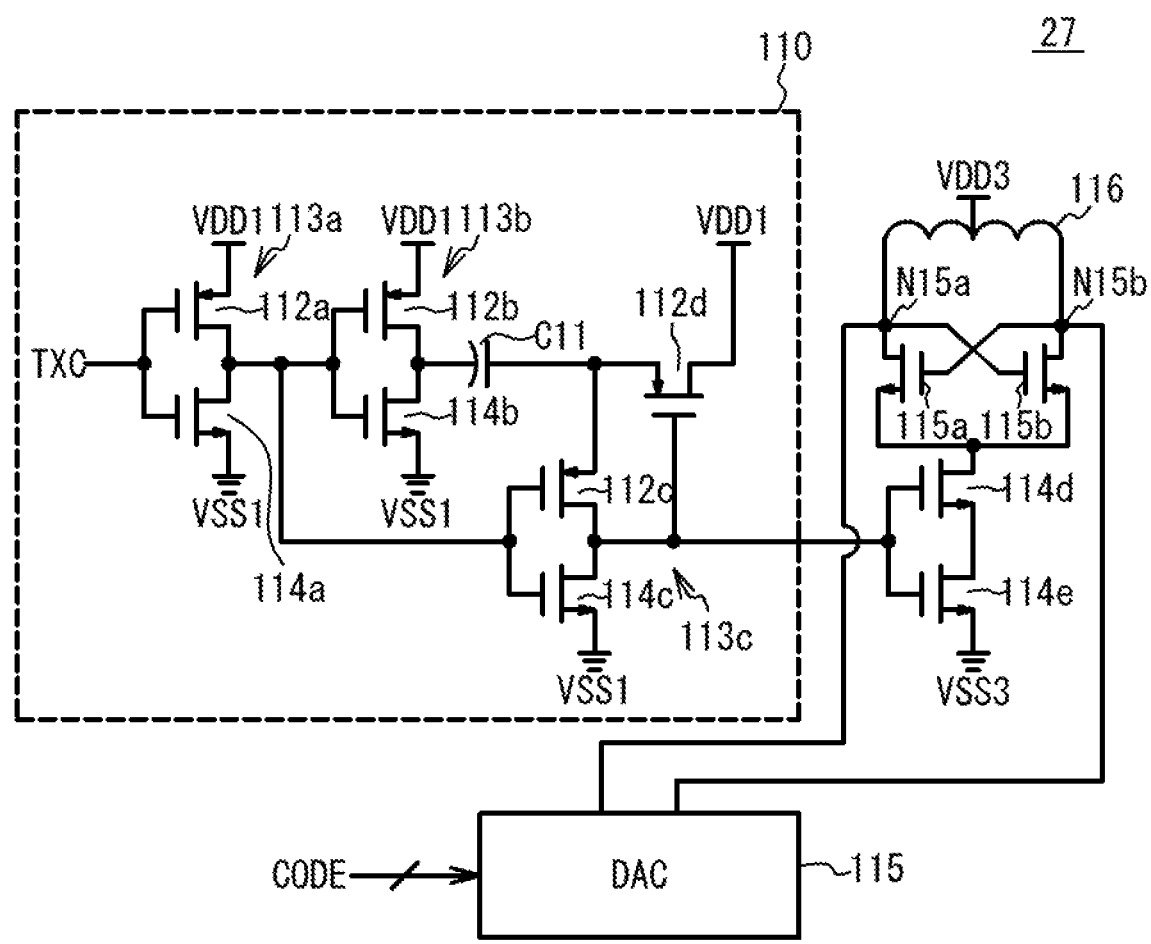
FIG. 24 is a circuit diagram of a transmission circuit in the third embodiment.

FIG. 24 is a circuit diagram of the transmission circuit in the third embodiment. As illustrated in FIG. 24, the transmission circuit 27 includes a booster circuit 110 and an antenna 116. The booster circuit 110 includes inverters 113a to 113c, a PFET 112d, and a capacitor C11. The inverter 113a includes a PFET 112a and an NFET 114a, the inverter 113b includes a PFET 112b and an NFET 114b, and the inverter 113c includes a PFET 112c and an NFET 114c.

When the control signal TXC is low level, the outputs of the inverters 113b and 113c are low level. The PFET 112d is turned ON. VSS1 is applied to one end of the capacitor C11, and VDD1 is applied to the other end of the capacitor C11. Thereby the capacitor C11 is charged. When the control signal TXC is high level, the outputs of the inverters 113b and 113c are high level. The PFET 112d is turned OFF. The sum of VDD1 and the difference between the voltages at both ends of the capacitor C11 is applied to the source of the PFET 112c of the inverter 113c. Thus, the output of the inverter 113c becomes higher than VDD1.

The voltage VDD3 is applied to a first end of the antenna 116, and second ends of the antenna 116 are connected to nodes N15a and N15b. The drains of NFETs 115a and 115b are respectively connected to the nodes N15a and N15b, and the gates of the NFETs 115a and 115b are respectively connected to the nodes N15b and N15a, and the sources of the NFETs 115a and 115b are connected to VSS3 through NFETs 114d and 114e. When the output of the booster circuit 110 becomes high level, the NFETs 114d and 114e are turned ON, and the high-frequency signal is output from the antenna 116. The leak current through the NFETs 114d and 114e is reduced by connecting in cascade the NFETs 114d and 114e.

The nodes N15a and N15b are connected to a digital analog convertor (DAC) 115. The DAC 115 includes a pull-down switch including a capacitor and an FET. When an 8-bit code is input to the DAC 115, the capacitance between the nodes N15a and N15b becomes the value corresponding to the code. This changes the frequency of the high-frequency signal output from the antenna 116 by the frequency corresponding to the code. The receive circuit that has received the high-frequency signal output from the antenna 116 is able to receive the code of the frequency of the high-frequency signal (i.e., the electromotive force of the power generation unit 20).

The measuring device 10a of the third embodiment was fabricated using the 65 nm node CMOS technology. The power generation unit 20 and the measuring circuit 22 were the same as the power generation unit 20 and the measuring circuit 22 of the second embodiment.

Figure 25:
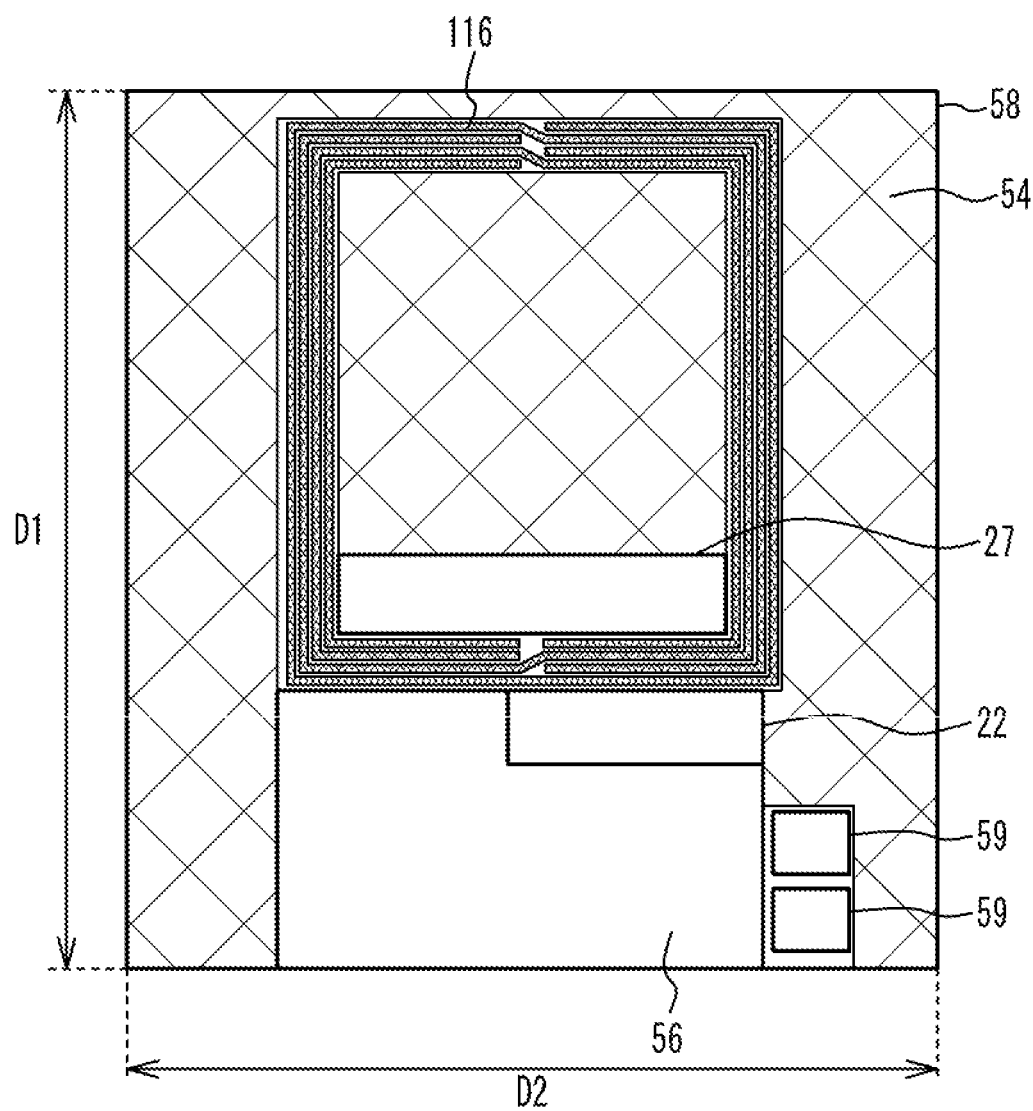
FIG. 25 is a plan view of a chip in the third embodiment.

FIG. 25 is a plan view of a chip in the third embodiment. A silicon (semiconductor) chip 58 includes the measuring circuit 22, the transmission circuit 27, the booster circuit 56, pads 59, and the antenna 116. The transmission circuit 27 is located within the antenna 116. The measuring circuit 22, the booster circuit 56, and the pad 59 are located in the outside of the antenna 116. Other regions of the chip 58 are solar cells 54. The power generation unit 20 is connected to the pads 59, and VDD1 and VSS1 are applied to the pads 59. The size of the chip 58 is D1×D2, and is 650 μm×635 μm.

Figure 26A:
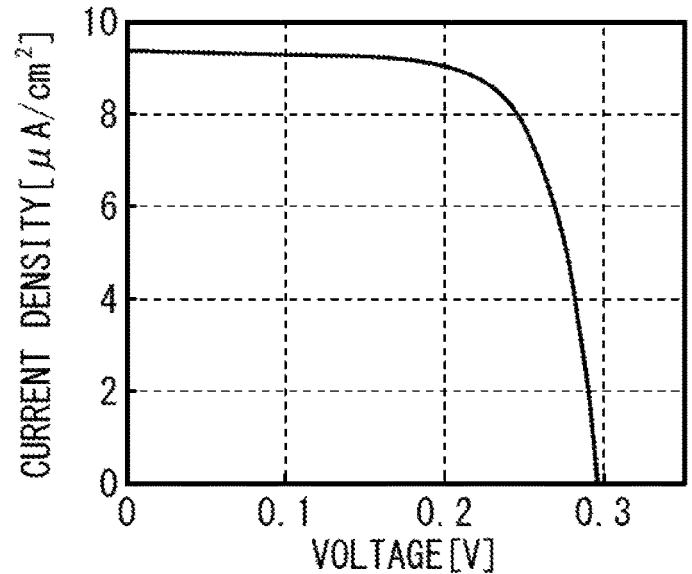
FIG. 26A to FIG. 26C illustrate the characteristics of a solar cell in the third embodiment.
Figure 26B:
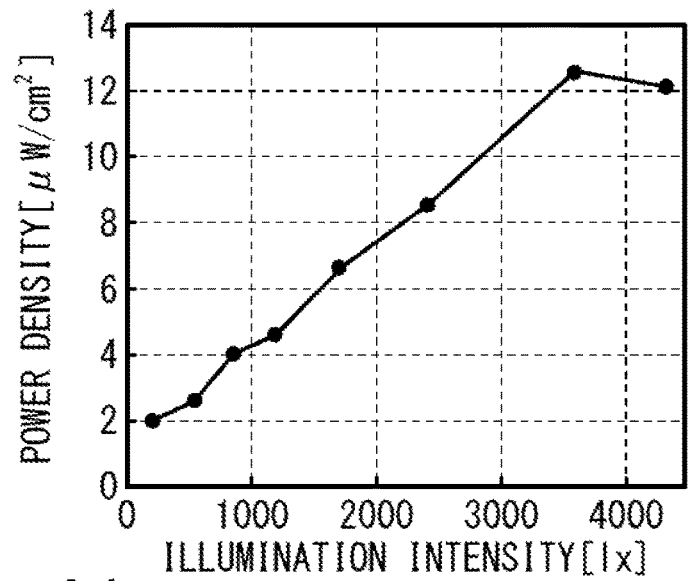
Figure 26C:
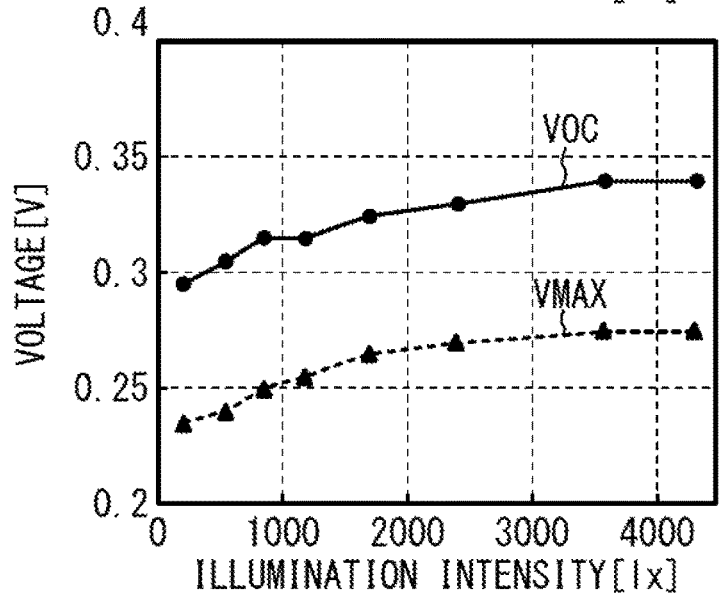

In the solar cell 54, three kinds of p-n junction solar cells are connected in parallel. FIG. 26A to FIG. 26C illustrate the characteristics of the solar cell in the third embodiment. FIG. 26A is a graph of current density versus voltage when the illumination intensity is 200 lx. At 0.2 V or less, a current density of approximately 9 μA/cm$^2$ is obtained. FIG. 26B is a graph of power density versus illumination intensity. Even when the illumination intensity is 200 lx, a power density of 1.97 μW/cm$^2$ is obtained. When the illumination intensity is 3500 lx or greater, a power density of 12 μW/cm$^2$ is obtained. FIG. 26C is a graph of circuit voltage VOC and maximum voltage VMAX versus illumination intensity. Even when the illumination intensity is 200 lx, VOC is 0.235 V and VMAX is 0.295 V. When the illumination intensity is 3500 lx or greater, VOC is 0.27 V, and VMAX is 0.34 V.

Figure 27A:
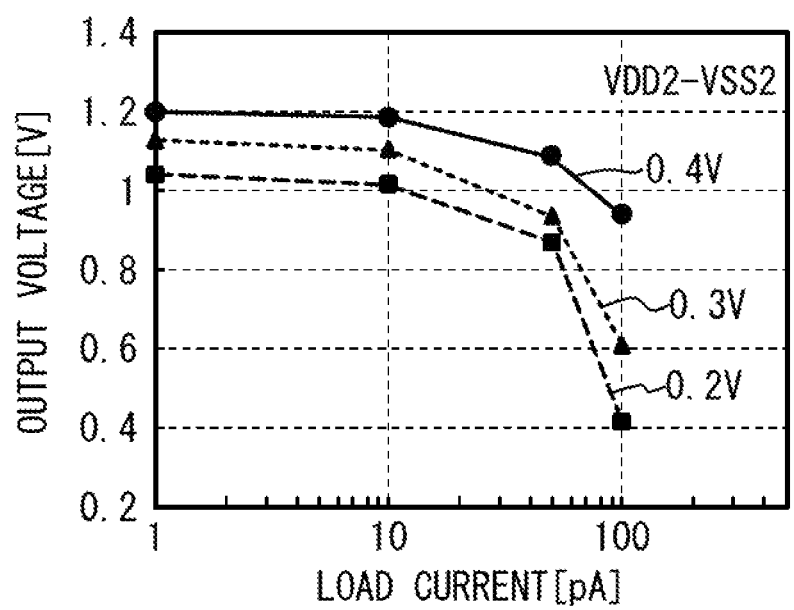
FIG. 27A and FIG. 27B illustrate the characteristics of the booster circuit in the third embodiment.
Figure 27B:
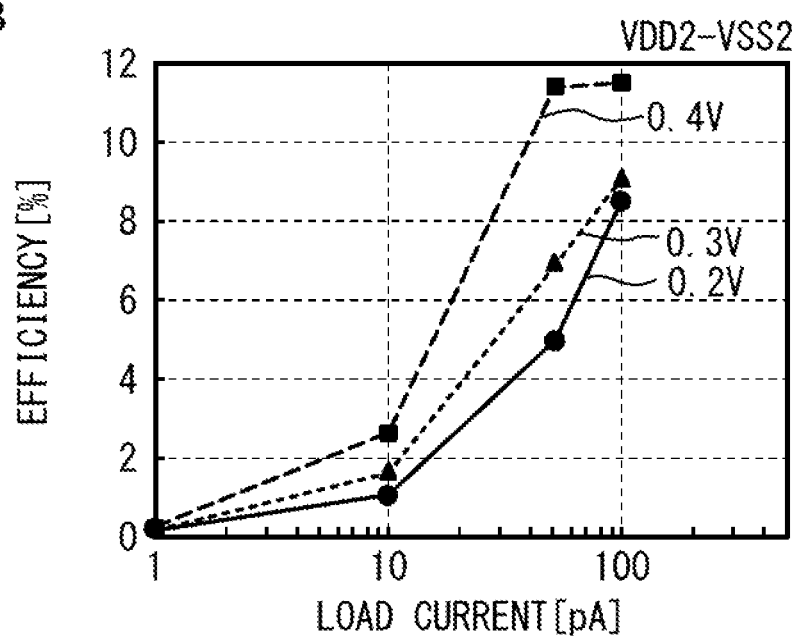

The capacitor C56 of the booster circuit 56 in FIG. 20 was a metal insulator metal (MIM) capacitor with 25 pF. FIG. 27A and FIG. 27B illustrate the characteristics of the booster circuit of the third embodiment. FIG. 27A is a graph of output voltage VDD3-VSS3 versus load current when VDD2-VSS2 is 0.2 V, 0.3 V, and 0.4 V. As illustrated in FIG. 27A, when the load current is 10 pA or less, the output voltage VDD3-VSS3 can be made to be 1 V or greater even at 0.2 V of VDD2-VSS2.

FIG. 27B is a graph of conversion efficiency versus load current when VDD2-VSS2 is 0.2 V, 0.3 V, and 0.4 V. As illustrated in FIG. 27B, when the load current is 10 pA and VDD2-VSS2 is 0.2 V, the conversion efficiency is 1% or greater.

In the third embodiment, the electric power other than the electric power for the measuring circuit 22 is supplied from the solar cell 54. As illustrated in FIG. 17C, the power consumption of the measuring circuit 22 is approximately 11 nW when the power-supply voltage VDD1-VSS1 is 800 mV. When it is assumed that the power density of the power generation unit 20 is 7 µW/cm², the area of the power generation unit 20 is 0.0016 cm². When it is assumed that the power consumption of the booster circuit 56 and the transmission circuit 27 is 5.3 nW, the area of the solar cell 54 is 0.27 mm² according to FIG. 26B. This is $\frac{1}{125}$ of the area of the power generation unit 20 when the electric power of the transmission circuit 27 is supplied from the power generation unit 20.

The area of each circuit in the chip 58 was as follows. The transmission circuit 27 was 0.010 mm², the booster circuit 56 was 0.034 mm², the measuring circuit 22 was 0.0047 mm², the solar cell 54 was 0.27 mm², and the total area was 0.3187 mm².

It may be considered to use a sugar sensor and an analog digital converter (ADC) in a measuring device for measuring sugars in the body fluid or bodily secretion of a living body. In this case, the power consumption of the sensor and the ADC is large, resulting in the large area of the power generation unit 20 using sugars. In addition, when the electric power for the sensor and the ADC is supplied from the power supply such as a solar cell, the area of the solar cell becomes large.

In the third embodiment, the measuring circuit 22 (a conversion circuit) that converts the electromotive force (a first electromotive force) VDD1-VSS1 of the power generation unit 20 into the code (a digital signal) uses the electromotive force of the power generation unit 20 as a power-supply voltage. The solar cell 54 (a power supply) supplies electric power to the transmission circuit 27 that transmits the information about the code using a wireless communication method, and does not supply the electric power to the measuring circuit 22.

As described above, the measuring circuit 22 that converts the electromotive force of the power generation unit 20 into the digital signal needs a small electricity and therefore is able to operate using the electromotive force of the power generation unit 20 as a power-supply voltage. On the other hand, the transmission circuit 27 consumes a large electric power, and therefore uses another power supply such as the solar cell 54. This reduces the size of the chip 58. As another power supply, instead of a photoelectric transducer such as the solar cell 54, a thermoelectric conversion device, or a capacitor or battery that stores electric power supplied from the outside can be used.

When the solar cell 54 is used as another power supply, the solar cell 54 can be mounted on the single chip 58 on which the measuring circuit 22, the booster circuit 56, and the transmission circuit 27 are also mounted using the CMOS technology.

When the measuring device is attached to the living body, there may be a case where the solar cell 54 does not generate power stably. For example, when the measuring device is attached to the contact lens 12 and the user blinks, the electric power generated by the solar cell 54 decreases. For example, when the measuring device is attached to, for example, a tooth in the mouth and the user closes their mouth, the electric power generated by the solar cell 54 decreases. Therefore, the electric power can be stably supplied to the transmission circuit 27 by providing the electricity storage device such as the capacitor C56 of the booster circuit 56.

The booster circuit 56 is activated according to the control signal HC (an activation signal) generated by the measuring circuit 22, and boosts the electromotive force (a second electromotive force) generated by the solar cell 54. Therefore, even when the power generation of the solar cell 54 is unstable, the booster circuit 56 can be activated.

An exemplary case where the transmission circuit 27 transmits the information about the code while the measuring device is attached to the living body is described, but the transmission circuit 27 may transmit the information about the code while the measuring device is detached from the living body as in the first and second embodiments. The measuring device 10a may include the memory circuit 24 of the first embodiment. In this case, the electric power of the memory circuit 24 is supplied from the power supply such as the solar cell 54.

FOURTH EMBODIMENT

Figure 28:
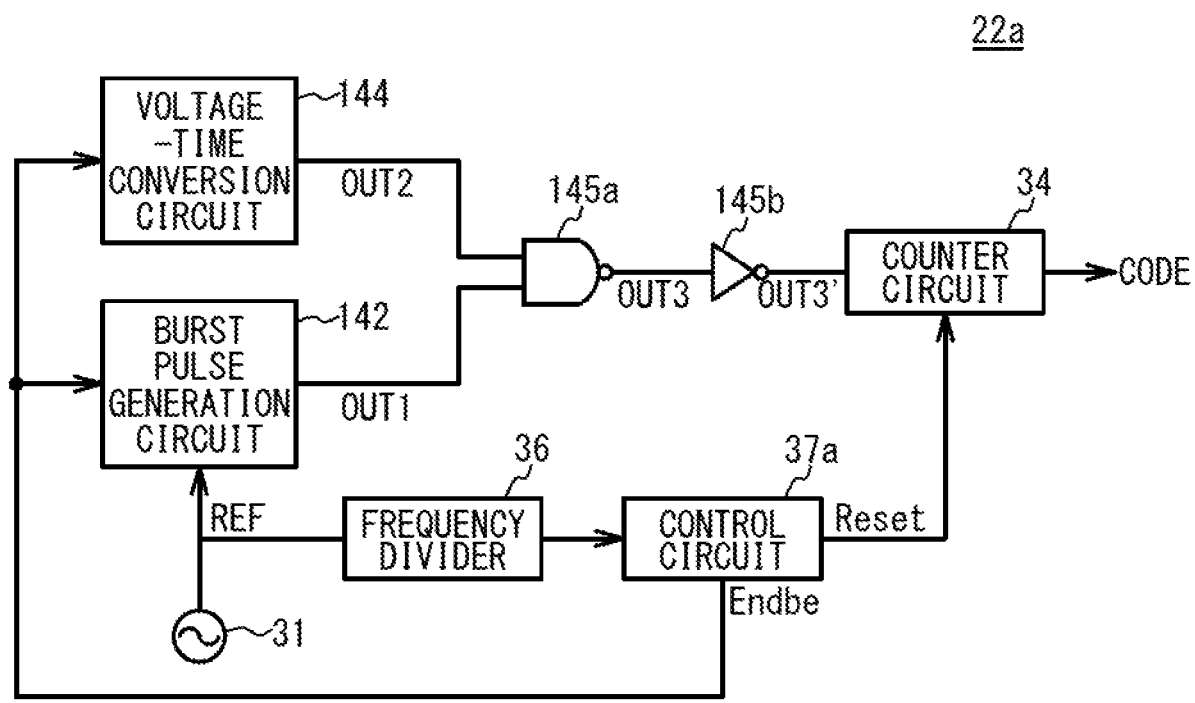
FIG. 28 is a block diagram of a measuring circuit in a fourth embodiment.

A fourth embodiment is another exemplary measuring circuit. FIG. 28 is a block diagram illustrating a measuring circuit in the fourth embodiment. As illustrated in FIG. 28, a measuring circuit 22a includes one oscillator 31. Like the oscillator 31 of the measuring circuit 22, the frequency of the oscillation signal REF of the oscillator 31 varies very little even when the power-supply voltage varies. The frequency divider 36 is identical to the frequency divider 36 in FIG. 5. A control circuit 37a includes the pulse generator 37 and the delay circuit 38 illustrated in FIG. 5, and generates the Reset signal and the Enable signal.

When the Enable signal becomes high level, a burst pulse generation circuit 142 generates a signal OUT1 from the oscillation signal REF. When the Enable signal becomes high level, a voltage-time conversion circuit 144 converts two voltages VDD-VSS into the period, and outputs a signal OUT2. A NAND circuit 145a outputs the NAND of the signals OUT1 and OUT2 as a signal OUT3. The inverter 145b outputs an inversion signal OUT3' of the signal OUT3 to the counter circuit 34. The counter circuit 34 is identical to the counter circuit 34 illustrated in FIG. 5, and counts the number of pulses of the signal OUT3' after the Reset signal is input, and outputs the number of counts as the code.

Figure 29:
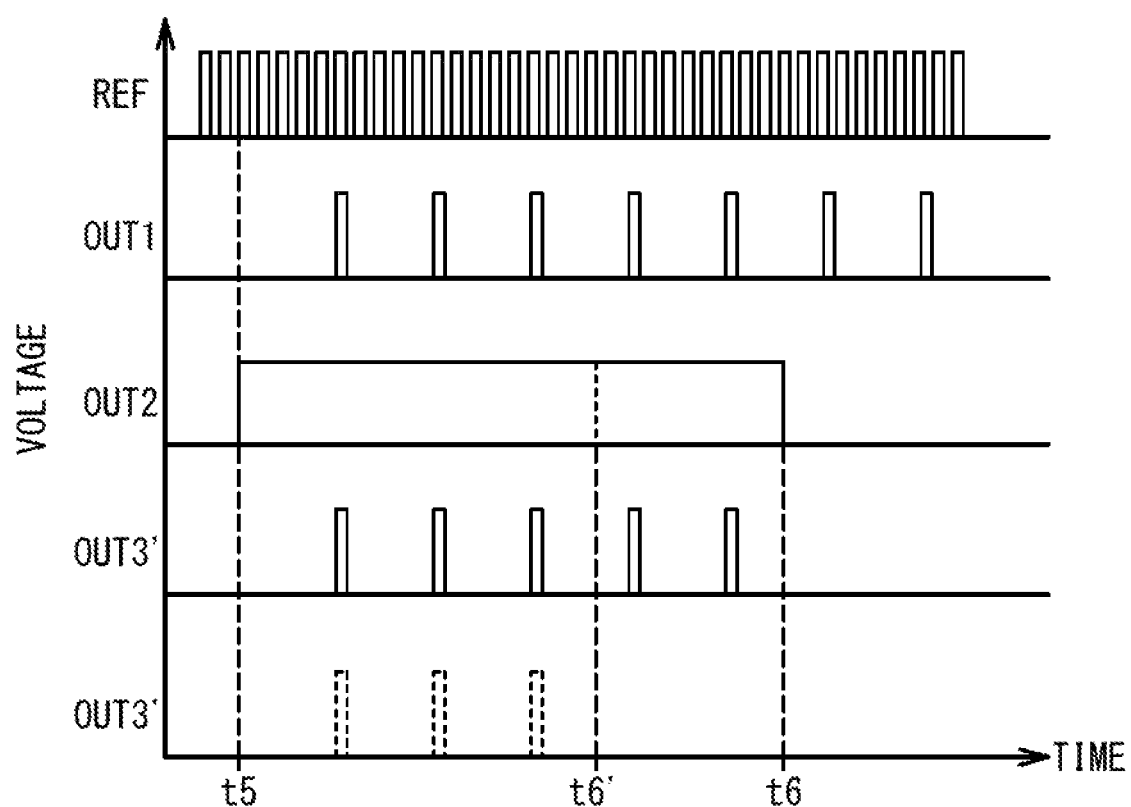
FIG. 29 illustrates the voltages of the signals of the measuring circuit with respect to time in the fourth embodiment.

FIG. 29 is a graph of the voltage of each signal of the measuring circuit versus time in the fourth embodiment. As illustrated in FIG. 29, the oscillator 31 outputs the oscillation signal REF. When the Reset signal is input at time t5, the burst pulse generation circuit 142 outputs a pulse as the signal OUT1 every fixed number of pulses of the oscillation signal REF. The voltage-time conversion circuit 144 outputs high level as the signal OUT2 from time t5 to time t6. The signal OUT3' becomes high level when high level is input as the signal OUT1 during the period when the signal OUT2 is high level (the period between time t5 and time t6). During other periods, the signal OUT3' is low level.

The counter circuit 34 counts the number of pulses of OUT3' between time t5 and time t6. The voltage-time conversion circuit 144 decreases the period during which high level is output as the electromotive force VDD-VSS of the power generation unit 20 decreases. For example, the signal OUT2 is high level from time t5 to time t6'. The pulse of the signal OUT3' is the pulse of the signal OUT1 between time t5 and time t6'. The number of pulses of OUT3' counted by the counter circuit 34 between time t5 and time t6' becomes less than the number of pulses of OUT3' between time t5 and time t6.

Accordingly, like the measuring circuit 22, the measuring circuit 22a is able to convert the electromotive force VDD-VSS of the power generation unit 20 into the code. The measuring circuit 22a can be replaced with the measuring circuit 22 in the first through third embodiments.

In the fourth embodiment, the voltage-time conversion circuit 144 uses the electromotive force VDD-VSS of the power generation unit 20 as a power-supply voltage, and converts the magnitude of VDD-VSS to a period. The counter circuit 34 uses VDD-VSS as a power-supply voltage, and counts the number of pulses of the oscillation signal REF within the period.

Therefore, the electromotive force that is an analog value can be converted into the number of pulses that is a digital value using the small power and low voltage generated by the power generation unit 20. Therefore, the power consumption of the measuring device 10 is further reduced.

The measuring circuit 22a in accordance with the fourth embodiment can be used instead of the measuring circuit 22 in the first through third embodiments.

Although preferred embodiments of the present invention have been described so far, the present invention is not limited to those particular embodiments, and various changes and modifications may be made to them within the scope of the invention claimed herein.

DESCRIPTION OF REFERENCE NUMERALS 10, 10a measuring device
12 contact lens
14 reception unit
16 container unit
20 power generation unit
22, 22a measuring circuit
23 timing circuit
24 memory circuit
26 transmission circuit
28 electricity storage device
30, 31 oscillator
32, 34 counter circuit
54 solar cell
56 booster circuit
60, 70, 70a, 70b antenna

The invention claimed is:

1. A measuring device comprising:
a power generation unit that generates an electromotive force through a reaction of biomolecules;
an oscillator that uses the electromotive force as a power-supply voltage and generates an oscillation signal;
a voltage-time conversion circuit that uses the electromotive force as a power-supply voltage and converts a magnitude of the electromotive force into a period; and
a counter circuit that uses the electromotive force as a power-supply voltage and counts the number of pulses of the oscillation signal within the period.

2. A container device comprising:
a container unit for storing a measuring device to be attached to a living body, the measuring device storing information about an amount of electric power generated using sugars in a body fluid or bodily secretion of the living body;
a first antenna and a second antenna, a third antenna in the measuring device to be sandwiched between the first antenna and the second antenna when the measuring device is stored in the container device; and
a reception unit that receives the information about the amount of electric power generated, which is stored in the measuring device, using a near-field wireless communication method when the measuring device is stored in the container unit,
wherein the measuring device transmits the information to the reception unit by the third antenna inhibiting electromagnetic coupling between the first antenna and the second antenna or propagation of an electromagnetic wave.

3. A measuring system comprising:
a measuring device that is attached to a living body, the measuring device including a power generation unit that generates an electromotive force through a reaction of biomolecules, a measuring circuit configured to generate information about the electromotive force and a memory circuit that stores the information about the electromotive force, the power generation unit supplying the electromotive force to the measuring circuit as a power-supply voltage with neither boosting of the electromotive force nor stepping down of the electromotive force; and
a container device for storing the measuring device, the container device receiving the information about the electromotive force, which is stored in the memory circuit, using a near-field wireless communication method when the measuring device is stored in the container device,
wherein the container device includes a first antenna and a second antenna,
wherein the measuring device includes a third antenna to be sandwiched between the first antenna and the second antenna when the measuring device is stored in the container device,
wherein the measuring device transmits the information to the container device by the third antenna inhibiting electromagnetic coupling between the first antenna and the second antenna or propagation of an electromagnetic wave.

4. A measuring system comprising:
a measuring device that is attached to a living body, the measuring device including a power generation unit that generates an electromotive force through a reaction of biomolecules, a measuring circuit configured to generate information about the electromotive force and a memory circuit that stores the information about the electromotive force, the power generation unit supplying the electromotive force to the measuring circuit as a power-supply voltage with neither boosting of the electromotive force nor stepping down of the electromotive force; and
a container device for storing the measuring device, the container device receiving the information about the electromotive force, which is stored in the memory circuit, using a near-field wireless communication method when the measuring device is stored in the container device,
wherein the measuring circuit includes:
a first oscillator that uses the electromotive force of the power generation unit as the power-supply voltage, and generates a first oscillation signal of which a period varies in response to a variation in the electromotive force,
a second oscillator that uses the electromotive force as a power-supply voltage and generates a second oscillation signal of which a variation in period with respect to a variation in the electromotive force is smaller than that of the first oscillator,
a timing circuit that uses the electromotive force as a power-supply voltage and generates a first timing and a second timing according to the second oscillation signal, and
a counter circuit that uses the electromotive force as a power-supply voltage, and counts the number of pulses of the first oscillation signal between the first timing and the second timing,
wherein the memory circuit stores the number of pulses as the information.

5. The measuring system according to claim 4, wherein the power generation unit generates the electromotive force using sugars in the body fluid or bodily secretion of the living body.

6. The measuring system according to claim 4, wherein the measuring device is mounted to a contact lens, and the biomolecules is a tear.

7. A measuring device comprising:
a power generation unit that generates an electromotive force through a reaction of biomolecules;
a first oscillator that uses the electromotive force as a power-supply voltage and generates a first oscillation signal of which a period varies in response to a variation in the electromotive force;
a second oscillator that uses the electromotive force as a power-supply voltage and generates a second oscillation signal of which a variation in period with respect to a variation in the electromotive force is smaller than that of the first oscillator; and
a timing circuit that uses the electromotive force as a power-supply voltage and generates a first timing and a second timing according to the second oscillation signal; and
a counter circuit that uses the electromotive force as a power-supply voltage and counts the number of pulses of the first oscillation signal between the first timing and the second timing.

8. The measuring device according to claim 7, further comprising a memory circuit that stores information on the number of pulses.

9. The measuring device according to claim 8, further comprising a transmission circuit that transmits the information about the number of pulses stored in the memory circuit using a near-field wireless communication method.

10. The measuring device according to claim 8, further comprising an electricity storage device that accumulates electric power generated by the power generation unit, and supplies an electric power for retaining the information about the number of pulses stored in the memory circuit to the memory circuit when the power generation unit does not generate electric power.

11. A measuring device to be attached to a living body, comprising:

a power generation unit that generates a first electromotive force using sugars in a body fluid or bodily secretion of the living body;
a conversion circuit that uses the first electromotive force as a power-supply voltage and converts the first electromotive force into a digital signal, the power generation unit supplying the first electromotive force to the conversion circuit as a power-supply voltage with neither boosting of the electromotive force nor stepping down of the first electromotive force;
a transmission circuit that transmits information about the digital signal using a wireless communication method; and
a power supply that supplies electric power to the transmission circuit and does not supply the electric power to the conversion circuit,
wherein the conversion circuit includes:
a first oscillator that uses the first electromotive force of the power generation unit as the power-supply voltage, and generates a first oscillation signal of which a period varies in response to a variation in the first electromotive force,
a second oscillator that uses the first electromotive force as a power-supply voltage and generates a second oscillation signal of which a variation in period with respect to a variation in the first electromotive force is smaller than that of the first oscillator,
a timing circuit that uses the first electromotive force as a power-supply voltage and generates a first timing and a second timing according to the second oscillation signal, and
a counter circuit that uses the first electromotive force as a power-supply voltage, counts the number of pulses of the first oscillation signal between the first timing and the second timing and outputs the number of pulses as the digital signal.

12. The measuring device according to claim 11, wherein the power supply is a solar cell.

13. The measuring device according to claim 12, further comprising a booster circuit that is activated according to an activation signal generated by the conversion circuit and boosts a second electromotive force generated by the solar cell.

14. The measuring device according to claim 11, wherein the power generation unit does not supply the first electromotive force to the transmission circuit.

* * * * *